United States Patent
Boileau et al.

(10) Patent No.: US 8,265,739 B1
(45) Date of Patent: Sep. 11, 2012

(54) SYSTEMS AND METHODS FOR DISTINGUISHING CARDIAC ISCHEMIA FROM SYSTEMIC INFLUENCES ON IEGM MORPHOLOGY USING AN IMPLANTABLE MEDICAL DEVICE

(75) Inventors: Peter Boileau, Valencia, CA (US);
Xiaoyi Min, Thousand Oaks, CA (US);
Jong Gill, Valencia, CA (US); Rupinder Bharmi, Canyon Country, CA (US);
Joseph J. Florio, Bend, OR (US);
Michael E. Benser, Valencia, CA (US);
Gene A. Bornzin, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 1093 days.

(21) Appl. No.: 12/016,166

(22) Filed: Jan. 17, 2008

Related U.S. Application Data

(60) Provisional application No. 60/885,674, filed on Jan. 19, 2007.

(51) Int. Cl.
*A61B 5/0402* (2006.01)
*A61B 5/0428* (2006.01)
*A61B 5/0452* (2006.01)

(52) U.S. Cl. ...................................... 600/516; 600/517
(58) Field of Classification Search .................. 600/516, 600/517; 607/25
See application file for complete search history.

(56) References Cited

U.S. PATENT DOCUMENTS

| | | | |
|---|---|---|---|
| 4,712,555 A | 12/1987 | Thornander et al. |
| 4,731,051 A | 3/1988 | Fischell |
| 4,788,980 A | 12/1988 | Mann et al. |
| 4,940,052 A | 7/1990 | Mann et al. |
| 4,944,298 A | 7/1990 | Sholder |
| 4,947,845 A | 8/1990 | Davis |
| 5,113,869 A | 5/1992 | Nappholz et al. |
| 5,135,004 A | 8/1992 | Adams et al. |
| 5,199,428 A | 4/1993 | Obel et al. |
| 5,203,326 A | 4/1993 | Collins |
| 5,313,953 A | 5/1994 | Yomtov et al. |
| 5,328,460 A | 7/1994 | Lord et al. |
| 5,466,254 A | 11/1995 | Helland |
| 5,476,483 A | 12/1995 | Bornzin et al. |
| 5,514,162 A | 5/1996 | Bornzin et al. |
| 5,531,768 A | 7/1996 | Alferness |
| 5,960,797 A | 10/1999 | Kramer et al. |
| 6,016,443 A | 1/2000 | Ekwall et al. |
| 6,021,350 A | 2/2000 | Mathson |

(Continued)

FOREIGN PATENT DOCUMENTS

EP 0721786 B1 6/1998

(Continued)

*Primary Examiner* — Tammie K Heller

(57) ABSTRACT

Techniques are provided for use in a pacemaker or implantable cardioverter/defibrillator (ICD) for distinguishing cardiac ischemia from other conditions affecting the morphology of electrical cardiac signals sensed within a patient, such as hypoglycemia, hyperglycemia or other systemic conditions. In one example, the device detects changes in morphological features of cardiac signals indicative of possible cardiac ischemia within the patient, such as changes in ST segment elevation within an intracardiac electrogram (IEGM). The device determines whether the changes in the morphological features are the result of spatially localized changes within a portion of the heart and then distinguishes cardiac ischemia from other conditions affecting the morphology of electrical cardiac signals based on that determination. In another example, the device exploits the interval between the peak of a T-wave (Tmax) and the end of the T-wave (Tend). A significant increase in the Tend–Tmax interval is indicative of ischemia rather than a systemic condition.

15 Claims, 22 Drawing Sheets

U.S. PATENT DOCUMENTS

| | | |
|---|---|---|
| 6,108,577 A | 8/2000 | Benser |
| 6,112,116 A | 8/2000 | Fischell et al. |
| 6,115,628 A | 9/2000 | Stadler et al. |
| 6,128,526 A | 10/2000 | Stadler et al. |
| 6,233,486 B1 | 5/2001 | Ekwall et al. |
| 6,249,705 B1 | 6/2001 | Snell |
| 6,256,538 B1 | 7/2001 | Ekwall |
| 6,264,606 B1 | 7/2001 | Ekwall et al. |
| 6,272,379 B1 | 8/2001 | Fischell et al. |
| 6,377,852 B1 | 4/2002 | Bornzin et al. |
| 6,381,493 B1 | 4/2002 | Stadler et al. |
| 6,468,263 B1 | 10/2002 | Fischell et al. |
| 6,501,983 B1 | 12/2002 | Natarajan et al. |
| 6,519,493 B1 | 2/2003 | Florio et al. |
| 6,609,023 B1 | 8/2003 | Fischell et al. |
| 6,985,771 B2 | 1/2006 | Fischell et al. |
| 7,107,096 B2 | 9/2006 | Fischell et al. |
| 7,142,911 B2 | 11/2006 | Boileau et al. |
| 7,225,015 B1 | 5/2007 | Min et al. |
| 7,272,436 B2 | 9/2007 | Gill et al. |
| 7,277,745 B2 | 10/2007 | Natarajan et al. |
| 7,297,114 B2 | 11/2007 | Gill et al. |
| 2002/0038091 A1 * | 3/2002 | Starobin et al. .............. 600/508 |
| 2002/0143265 A1 | 10/2002 | Ackerman et al. |
| 2004/0077962 A1 | 4/2004 | Kroll |
| 2008/0082135 A1 * | 4/2008 | Arcot-Krishnamurthy et al. ................................. 607/9 |

FOREIGN PATENT DOCUMENTS

| | | |
|---|---|---|
| EP | 0867146 B1 | 2/2004 |
| WO | 9216257 | 10/1992 |

* cited by examiner

SYSTEMS AND METHODS FOR DISTINGUISHING CARDIAC ISCHEMIA FROM SYSTEMIC INFLUENCES ON IEGM MORPHOLOGY USING AN IMPLANTABLE MEDICAL DEVICE

RELATED APPLICATIONS

This patent application claims benefit from U.S. Provisional Application Ser. No. 60/885,674, filed Jan. 19, 2007, of Boileau et al., which is incorporated by reference herein.

FIELD OF THE INVENTION

The invention generally relates to implantable medical devices such as pacemakers and implantable cardioverter/defibrillators (ICDs) and, in particular, to techniques for detecting cardiac ischemia and distinguishing cardiac ischemia from systemic influences on intracardiac electrogram (IEGM) signal morphology using such devices.

BACKGROUND OF THE INVENTION

Cardiac ischemia is a condition whereby heart tissue does not receive adequate amounts of oxygen and is usually caused by a blockage of an artery leading to heart tissue. If sufficiently severe, cardiac ischemia results in an acute myocardial infarction (AMI), also referred to as a heart attack. With AMI, a substantial portion of heart muscle ceases to function because it no longer receives oxygen, usually due to significant blockage of the coronary artery. Generally, AMI occurs when plaque (such as fat, cholesterol, and calcium) builds up and then ruptures in the coronary artery, allowing a blood clot or thrombus to form. Eventually, the blood clot completely blocks the coronary artery and so heart tissue beyond the blockage no longer receives oxygen and the tissue dies. In many cases, an AMI proves fatal because too much tissue is damaged to allow continued functioning of the heart muscle. Indeed, AMI is a leading cause of death here in the United States and worldwide. In other cases, although the AMI itself is not fatal, it strikes while the victim is engaged in potentially dangerous activities, such as driving vehicles or flying airplanes, and the severe pain and possible loss of consciousness associated with AMI results in fatal accidents. Even if the victim survives the AMI, quality of life may thereafter be severely restricted.

Often AMI is preceded by episodes of cardiac ischemia that are not sufficiently serious to cause actual permanent injury to the heart tissue. Nevertheless, these episodes are often precursors to AMI. Episodes of cardiac ischemia may also trigger certain types of arrhythmias that may prove fatal, particularly ventricular fibrillation (VF) wherein the ventricles of the heart beat chaotically, resulting in little or no net flow of blood from the heart to the brain and other organs. Indeed, serious episodes of cardiac ischemia (referred to herein as acute myocardial ischemia) typically result in either a subsequent AMI or VF, often within one to twenty-four four hours, sometimes within only a half an hour or less. Accordingly, it would be highly desirable to provide a technique for reliably detecting cardiac ischemia in real-time so that the victim may be warned and medical attention sought. If properly warned, surgical procedures may be implemented to locate and remove the growing arterial blockage or anti-thrombolytic medications may be administered. At the very least, such warnings would allow the victim to cease activities that might result in a fatal accident. Moreover, in many cases, AMI or VF is triggered by strenuous physical activities and so ischemia warnings would allow the victim to cease such activities, possibly preventing AMP or VF from occurring.

Many patients at risk of cardiac ischemia have pacemakers, ICDs or other medical devices implanted therein, or are candidates for such devices. Accordingly, techniques have been developed for detecting cardiac ischemia using implanted medical devices. In particular, techniques have been developed for analyzing intracardiac electrogram (IEGM) signals sensed by such devices in an effort to detect cardiac ischemia. See, for example, U.S. Pat. No. 6,108,577 to Benser, entitled "Method and Apparatus for Detecting Changes in Electrocardiogram Signals." See, also, U.S. Pat. Nos. 5,113,869 to Nappholz; 5,135,004 to Adams et al.; 5,199,428 to Obel et al.; 5,203,326 to Collins; 5,313,953 to Yomtov et al; 6,501,983 to Natarajan et al.; 6,016,443, 6,233,486, 6,256,538, and 6,264,606 to Ekwall; 6,021,350 to Mathson; 6,112,116 and 6,272,379 to Fischell et al; 6,128,526, 6,115,628 and 6,381,493 to Stadler et al; and. Many IEGM-based ischemia detection techniques seek to detect ischemia by identifying changes in the elevation of the ST segment of the IEGM that occur during cardiac ischemia. The ST segment represents the portion of the cardiac signal between ventricular depolarization (also referred to as an R-wave or QRS complex) and ventricular repolarization (also referred to as a T-wave). Herein, the ST segment elevation pertains to the amplitude of the ST segment relative to some isoelectric baseline and hence can be positive or negative. Moreover, the elevation can increase or decrease relative to the baseline due to ischemia or other factors. A change in the ST segment elevation (which may also be referred to as an ST segment deviation) is typically measured relative to a historical elevation baseline. Note that the QRS complex usually follows an atrial depolarization (also referred to as a P-wave.) P-waves, R-waves and T-waves are also regarded as features of a surface electrocardiogram (EKG). For convenience and generality, the terms P-wave, T-wave and T-wave are used herein to refer to the corresponding features of internal cardiac signals, i.e. IEGMs.

Typically, with ST-based techniques, the amount of deviation, if any, from a baseline ST segment elevation is compared by the implanted device against a predetermined threshold. If the amount of deviation exceeds the threshold, cardiac ischemia is deemed to have occurred. Warning signals may be generated and, in at least some devices, therapy may be automatically adjusted in response to the ischemia. Often, the threshold is set by the physician during a programming session following device implant but is not otherwise adjusted. Although ST segment elevation is often exploited, other parameters derived from morphological features of the IEGM can instead be used. Other parameters that potentially may be exploited to detect cardiac ischemia include various duration-based parameters such as P-wave width, QRS-complex width and T-wave width; various slope-based parameters such as maximum P-wave slope, maximum QRS-complex slope and maximum T-wave slope; various amplitude-based parameters such as peak P-wave amplitude, peak QRS-complex amplitude and peak T-wave amplitude; as well as various interval-based parameters such as atrioventricular (AV) intervals and the aforementioned ST intervals. Also, devices may exploit the interval between the beginning of a QRS complex and the maximum amplitude (i.e. the peak) of a corresponding T-wave as well as the interval between the beginning of the QRS complex and the end of the corresponding T-wave. These intervals are referred to herein, respectively, as the QTmax interval and the QTend interval. For further discussions regarding various intervals that may be appropriate, alone or in combination with one another, for detecting cardiac ischemia, see U.S. patent application Ser. No. 11/394, 724, of Ke et al., filed Mar. 31, 2006, entitled "Ischemia Detection using T-wave Amplitude, QTmax and ST Segment Elevation and Pattern Classification Techniques." See, also, U.S. Pat. Nos. 7,107,096; 6,985,771; 6,609,023; 6,468,263; 6,272,379; and 6,112,116, each to Fischell et al.

Although the detection of cardiac ischemia is of paramount importance since ischemia may be a precursor to a potentially fatal AMI or VF, it is also desirable to detect hypoglycemia, hyperglycemia, or other abnormal physiological conditions so as to provide suitable warning signals. Diabetic patients, particular, need to frequently monitor blood glucose levels to ensure that the levels remain within acceptable bounds and, for insulin dependent diabetics, to determine the amount of insulin that must be administered. Various techniques have been developed for detecting hypoglycemia and hyperglycemia based on features of electrical cardiac signals, particularly ST segments and T-waves. See, for example, U.S. patent application Ser. No. 11/043,612, of Gill et al., filed Jan. 25, 2005, entitled "System and Method for Distinguishing Among Ischemia, Hypoglycemia and Hyperglycemia Using an Implantable Medical Device." See, also, U.S. Pat. Nos. 7,272,436 and 7,297,114, to Gill et al., also entitled "System and Method for Distinguishing Among Ischemia, Hypoglycemia and Hyperglycemia Using an Implantable Medical Device." See, also, U.S. patent application Ser. No. 11/127,370, of Bharmi, filed May 11, 2005, entitled "System and Method for Distinguishing Between Hypoglycemia and Hyperglycemia Using an Implantable Medical Device" (which is a CIP of application Ser. No. 11/043,612) and U.S. patent application Ser. No. 11/117,624, also of Bharmi, filed Apr. 27, 2005, entitled "System and Method for Detecting Hypoglycemia Based on a Paced Depolarization Integral Using an Implantable Medical Device." A technique for detecting cardiac ischemia based on T-waves is set forth in U.S. Pat. No. 7,225,015, entitled "System and Method for Detecting Cardiac Ischemia Based on T-Waves Using an Implantable Medical Device", to Min et al. See, also, U.S. patent application Ser. No. 11/740,175, of Fard et al., filed Apr. 25, 2007, entitled "System and Method for Efficiently Distinguishing among Cardiac Ischemia, Hypoglycemia and Hyperglycemia using an Implantable Medical Device and an External System."

Accordingly, it would be also desirable to provide improved techniques for detecting cardiac ischemia and distinguishing cardiac ischemia from hypoglycemia, hyperglycemia or other systemic influences on IEGM morphology and it is to this end that various aspects of the present invention are directed.

SUMMARY OF THE INVENTION

In accordance with a first exemplary embodiment, a method is provided for use with an implantable medical device such as a pacemaker or ICD for distinguishing cardiac ischemia from other conditions affecting the morphology of electrical cardiac signals sensed within a patient, such as hypoglycemia, hyperglycemia or other systemic conditions. Briefly, the device detects changes in morphological features of electrical cardiac signals indicative of possible cardiac ischemia within the patient, such as changes in ST segment elevation within an IEGM. The device determines whether the changes in the morphological features are the result of spatially localized changes within a portion of the heart and then distinguishes cardiac ischemia from other conditions affecting the morphology of electrical cardiac signals based on whether the changes in the morphological features are the result of such spatially localized changes. In this regard, cardiac ischemia is typically spatially localized within only a portion of the heart; whereas systemic conditions affecting IEGM morphology, such as hypo/hyperglycemia, are not spatially localized. Hence, changes to an IEGM caused by ischemia are distinguishable from changes caused by systemic conditions based, at least in part, on whether changes to the IEGM are consistent with spatially localized changes in the heart or are instead consistent with global influences.

In a first illustrative implementation, the implantable device determines whether the changes in the morphological features are the result of spatially localized changes within a portion of the heart by first determining whether changes in the detected features are manifest both in features affected by atrial repolarization and in features affected by ventricular repolarization. Then, the device determines that the changes in the detected features are global if changes are detected both in features affected by atrial repolarization and in features affected by ventricular repolarization. In contrast, the device instead determines that the changes in the detected features are local if the changes are manifest either in the features affected by atrial repolarization or in the features affected by ventricular repolarization, but not both. In one particular example, the device detects changes in the elevation of the PR segment (which is primarily affected by atrial repolarization) and the ST segment (which is primarily affected by ventricular repolarization). If significant changes are detected both in the elevation of the PR segment and in the elevation of the ST segment, then the changes are deemed to be "global" and hence are indicative of a systemic condition such as hypo/hyperglycemia. However, if significant changes are detected either in the elevation of the PR segment, or in the elevation of the ST segment, but not both, then the changes are instead deemed to be "local" and hence are indicative of cardiac ischemia. Note that "global" and "local" are relative terms. Changes deemed to be "global" need not be absolutely global; changes deemed to be "local" need not be absolutely local.

In a second illustrative implementation, the implantable device determines whether the changes in the morphological features are the result of spatially localized changes within a portion of the heart by first determining whether changes in the detected features are manifest both in bipolar signals sensed at a first location in the heart (such as the atria) and in unipolar signals sensed at a second, different location in the heart (such as the right ventricle). Then, the device determines that the changes in the detected features are global if changes are detected in both of the signals. In contrast, the device instead determines that the changes in the detected features are local if significant changes are detected only within the atrial bipolar signals, or within the unipolar ventricular signals, but not both. In one particular example, the device detects changes, if any, in ST segment elevations (or in other repolarization characteristics indicative of a possible ischemia.) If significant changes are detected in the elevation of the ST segment in both the atrial and the ventricular signals, then the changes are deemed to be "global" and hence are indicative of a systemic condition such as hypo/hyperglycemia. However, if changes in ST segment elevation are more significant in one of the signals but not the other, then the changes are deemed to be "local" and hence are indicative of cardiac ischemia. Alternatively, rather than exploiting bipolar atrial vs. unipolar ventricular signals, the device can instead exploit bipolar atrial vs. bipolar ventricular signals or two bipolar signals obtained at different locations within the ventricles, such as one in the RV and the other in the LV.

In a third illustrative implementation, the implantable device determines whether the changes in the morphological features are the result of spatially localized changes within a portion of the heart by first determining whether changes in the detected features are manifest in any or all of a plurality of combinations of signals sensed at a various locations in the heart. Then, the device determines that the changes in the detected features are global if changes are detected in all of the signals. In contrast, the device instead determines that the changes in the detected features are local if significant changes are detected only some of the signals. In one particular example, the device detects changes, if any, in ST segment elevations (or in other repolarization characteristics indicative of a possible ischemia.) If significant changes are detected in the elevation of the ST segment in all of the signals, then the changes are deemed to be "global" and hence are indicative of a systemic condition such as hypo/hyperglycemia. However, if significant changes in ST segment elevation are observed in only some of the signals, then the changes are deemed to be "local" and hence are indicative of cardiac ischemia.

If the device determines that the changes to the IEGM are not due to ischemia but are instead due to a systemic condition such as hypo/hyperglycemia, the device preferably then specifies the particularly systemic condition by exploiting various combinations of morphological parameters. In this regard, a wide variety of parameters may be used, depending upon the particular systemic condition to be detected. In addition to changes in ST segment and PR segment elevations, other parameters that potentially may be exploited to detect and distinguish various systemic conditions include duration-based parameters such as P-wave width, QRS-complex width and T-wave width; slope-based parameters such as maximum P-wave slope, maximum QRS-complex slope and maximum T-wave slope; amplitude-based parameters such as peak P-wave amplitude, peak QRS-complex amplitude and peak T-wave amplitude; as well as various interval-based parameters such as atrioventricular (AV) intervals, and the aforementioned QTmax and QTend intervals.

Upon detection of the onset of an episode of cardiac ischemia or other abnormal physiological condition, appropriate warning signals are generated, which can include both "tickle warning" signals applied to subcutaneous tissue and short range telemetry warning signals transmitted to a device external to the patient. Therapy may also be applied or modified by the implanted system in response to the detected condition, depending upon the capabilities of the implanted system. For example, if the implanted system is equipped with a drug pump, appropriate medications may be administered such as anti-thrombolytic drugs for ischemia or insulin for hyperglycemia. If overdrive pacing is being applied by the system, overdrive pacing is preferably deactivated to prevent the increased heart rate associated with overdrive pacing from exacerbating the ischemia. If the system has defibrillation capabilities, the system may immediately begin charging defibrillation capacitors upon detection of cardiac ischemia to permit prompt delivery of a defibrillation shock if the ischemia triggers VF. Additionally, or in the alternative, diagnostic information pertaining to the detected condition may be stored for subsequent review by a physician.

In accordance with a second exemplary embodiment, a method is provided for use with an implantable medical device such as a pacemaker or ICD for detecting cardiac ischemia and for distinguishing cardiac ischemia from other conditions affecting the morphology of electrical cardiac signals based, at least in part, on the interval between the peak of a T-wave (Tmax) and the end of the T-wave (Tend). Briefly, the device tracks repolarization peak-based intervals representative of intervals between the peaks of repolarization events and the ends of repolarization events within electrical cardiac signals such as IEGMs. The, device detects an episode of cardiac ischemia based on a significant increase in the repolarization peak-based intervals. That is, a significant increase in the Tend–Tmax interval is indicative of cardiac ischemia (e.g. if $\Delta$Tend–Tmax is found to be greater than a predetermined ischemia detection threshold). The T-wave-based technique may be used to confirm detection of ischemia made using the spatial localization technique, summarized above, or vice versa. Also, Tend–Tmax is largely unaffected by hypoglycemia or hyperglycemia, and hence Tend–Tmax can also be used to help distinguish ischemia from hypoglycemia or hyperglycemia so that appropriate therapy and/or warnings can be provided to the patient.

Hence, improved techniques are provided for detecting cardiac ischemia and distinguishing ischemia from systemic influences on cardiac signals morphology. The techniques are preferably performed by the implanted medical device itself to provide prompt warnings of abnormal conditions and to deliver appropriate therapy. Alternatively, the techniques may be performed by external devices, such as bedside monitors or the like, based on IEGM signals detected by the implanted device and transmitted to the external device. System and method implementations of the techniques are described herein.

BRIEF DESCRIPTION OF THE DRAWINGS

The above and further features, advantages and benefits of the present invention will be apparent upon consideration of the present description taken in conjunction with the accompanying drawings, in which:

FIGS. 5-1 and 5-2 set forth exemplary IEGMs illustrating spatially localized variations in IEGMs due to cardiac ischemia, and particularly illustrating the lack of any significant changes in PR segment elevation during ischemia induced in the ventricles, which are exploited by the discrimination technique of FIG. 3;

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators are used to refer to like parts or elements throughout.

Overview of Implantable System

Figure 1:
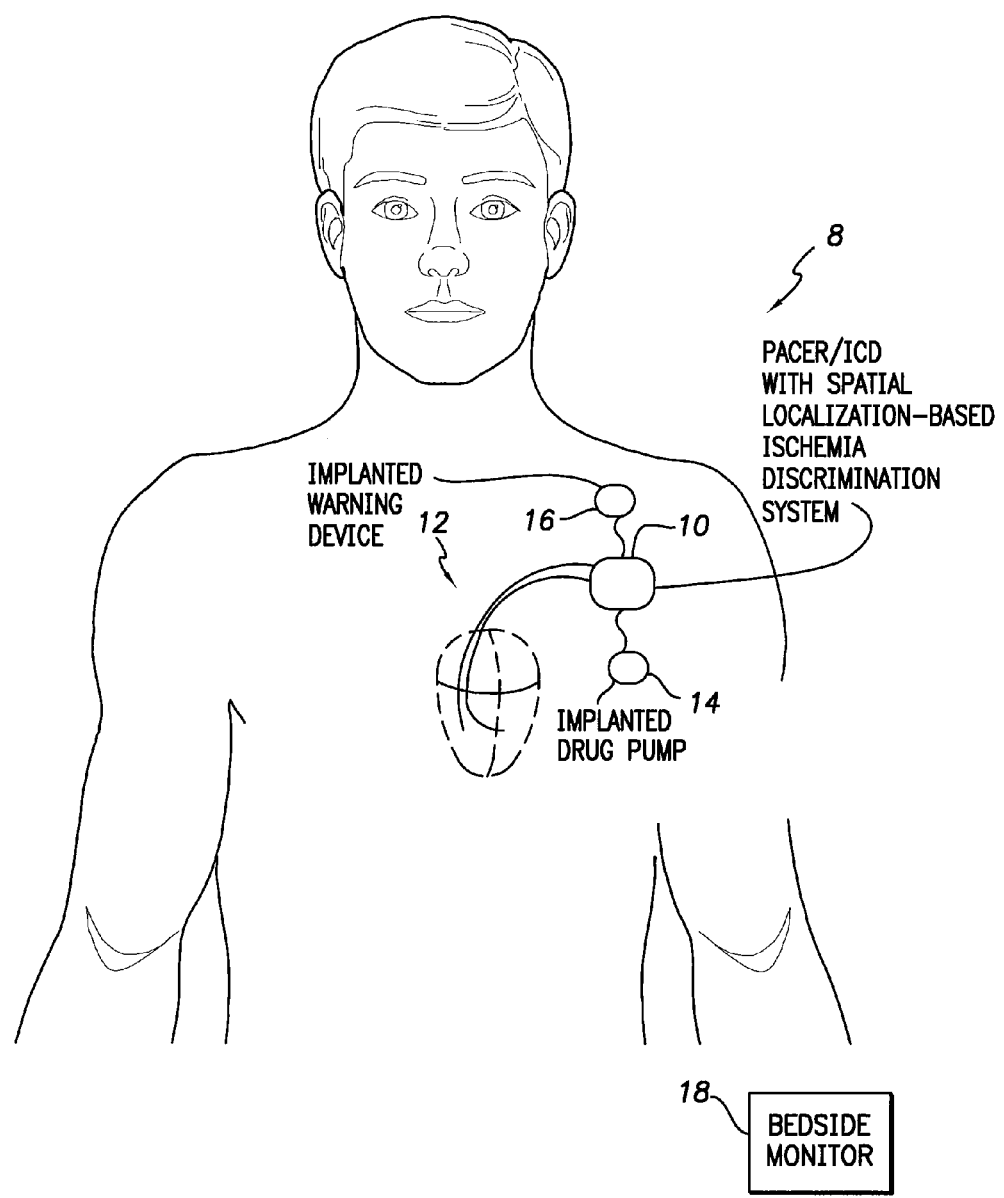
FIG. 1 illustrates pertinent components of an implantable medical system having a pacemaker or ICD capable of detecting cardiac ischemia and distinguishing ischemia from other abnormal physiological conditions based, in one example, on spatial localization of changes in IEGM signal morphology and, in another example, on changes in repolarization peak-based intervals.

FIG. 1 illustrates an implantable medical system 8 capable of detecting cardiac ischemia and distinguishing ischemia from other abnormal physiological conditions such as hypoglycemia or hyperglycemia. To this end, system 8 includes a pacer/ICD 10 or other cardiac stimulation device equipped with a spatial localization-based ischemia detection and discrimination system and/or a repolarization interval-based ischemia detection and discrimination system. The pacer/ICD also includes internal components for controlling the delivery of therapy and warnings in response to the detection of ischemia or other abnormal physiological conditions. To detect ischemia or other abnormal physiological conditions, pacer/ICD 10 senses one or more IEGM signals or other electrical cardiac signals, identifies changes in morphological parameters of the IEGMs indicative of a possible ischemia and then, in one example, discriminates ischemia from other conditions based on spatial localization of the changes in the IEGMs. In another example, the pacer/ICD instead discriminates ischemia based, at least in part, on changes Tend–Tmax intervals within the IEGM. Preferably, the device is equipped to perform both techniques so as to improve specificity. To detect the IEGMs, the pacer/ICD receives electrical cardiac signals from a set of cardiac pacing/sensing leads 12 implanted on or within the heart of the patient from which one or more IEGM signals is derived. In FIG. 1, only two pacing leads are shown. A more complete set of pacing leads is shown in FIG. 20, discussed below. The various ischemia detection and discrimination techniques used by the pacer/ICD to analyze the IEGM signals are explained in detail with reference to FIGS. 2-19.

If cardiac ischemia or another abnormal physiological condition is detected, appropriate therapy may be automatically delivered by the implantable system under the control of the pacer/ICD. For example, for ischemia, anti-thrombolytics or other appropriate medications may be automatically delivered directly to the patient via an implanted drug pump 14, if one is provided. Implantable devices for delivering anti-thrombolytic drugs are discussed in U.S. Pat. No. 5,960,797 to Kramer et al. The pacer/ICD may also change pacing parameters in response to the detection of ischemia to, for example, deactivate overdrive pacing, which may exacerbate the ischemia. Other forms of elevated pacing may be discontinued as well, such as atrial fibrillation (AF) suppression therapy or activity-based rate responsive pacing. Also, because myocardial perfusion occurs during diastole, the device might alter pacing therapy in response to detection of ischemia by reducing the pacing rate. If the rhythm is intrinsic, the hemodynamically effective heart rate might be slowed in response to ischemia detection by application of the special pacing technique described in U.S. Pat. No. 6,377,852 to Bornzin et al. Various other techniques for controlling delivery of therapy in response to ischemia are discussed in U.S. Pat. No. 6,256,538 to Ekwall, listed above. In addition, if the device is an ICD, then it may be controlled to immediately begin charging defibrillation capacitors in expectation of delivery of a defibrillation shock, which may be needed if the ischemia triggers VF. This is particularly appropriate if the ischemia is severe. As another example, for hypoglycemia, the device may use a drug pump to deliver insulin, particularly if the patient is known to be diabetic. Techniques for controlling delivery of therapy in response to hypoglycemia are set forth in U.S. Patent Application Serial Number 2004/0077962 of Kroll, published Apr. 22, 2004, entitled "System and Method for Monitoring Blood Glucose Levels Using an Implantable Medical Device." Information regarding implantable insulin pumps may be found in U.S. Pat. No. 4,731,051 to Fischell and in U.S. Pat. No. 4,947,845 to Davis.

Warning signals may additionally, or alternatively, be generated. For example, if ischemia is detected, the patient is warned by application of an internal perceptible "tickle" notification signal using an implanted warning device 16. "Tickle" warning device are discussed in U.S. Pat. No. 5,328,460 to Lord et al., entitled "Implantable Medication Infusion Pump Including Self-Contained Acoustic Fault Detection Apparatus." If the device is configured to generate warning signals for other conditions, such as hyperglycemia or hypoglycemia, the device preferably employs different notification signal frequencies for the different warnings so that the patient can properly distinguish between different warnings. In addition, warning signals may be transmitted using a short-range telemetry system to a bedside monitor 18 or to a handheld warning device (not separately shown) using techniques described within U.S. patent application Ser. No. 10/603,429, entitled "System And Method For Detecting Cardiac Ischemia Using an Implantable Medical Device", of Wang et al. The bedside monitor or handheld warning device provides audible or visual alarm signals to alert the patient, as well as textual or graphic displays. The bedside monitor or handheld warning device thereby provides confirmation of the warning to the patient, who may be otherwise uncertain as to the reason for the internally generated tickle warning signal.

In addition, once an abnormal physiological condition has been detected, diagnostic information is generated within the pacer/ICD for transmission to the bedside monitor or for subsequent transmission to an external programmer (not shown in FIG. 1) for review by a physician or other medical professional. The physician may then prescribe any other appropriate therapies to prevent additional episodes of the abnormal condition. The physician may also adjust the operation of the pacer/ICD to activate, deactivate or otherwise control any therapies that are automatically applied. The bedside monitor may be directly networked with a centralized computing system, such as the HouseCall™ system of St. Jude Medical, for immediately notifying the physician of the abnormal condition, particular if it appears dangerous, such as if the ischemia is an acute myocardial ischemia. Networking techniques for use with implantable medical systems are set forth, for example, in U.S. Pat. No. 6,249,705 to Snell, entitled "Distributed Network System for Use with Implantable Medical Devices." Note that a lower internal detection threshold may be used to trigger recording of diagnostics, with a higher threshold used for triggering warnings, and a still higher threshold for triggering automatic delivery of therapy.

Hence, FIG. 1 provides an overview of an implantable system having a detection and discrimination system for detecting and discriminating cardiac ischemia, hypoglycemia, hyperglycemia or other abnormal physiological conditions and for delivering appropriate therapy or warnings. Systems provided in accordance with the invention need not include all the components shown in FIG. 1. In many cases, for example, the system will include only the pacer/ICD and its leads. Drug pumps and warning devices are not necessarily implanted. In addition, although internal signal transmission lines are illustrated in FIG. 1 for interconnecting the various implanted components, wireless signal transmission may alternatively be employed. Furthermore, the particular locations, orientations and relative sizes of the implanted components shown in FIG. 1 are merely illustrative and may not necessarily correspond to actual implant locations, orientations or relative sizes.

Overview of the Spatial Localization-Based Detection Technique

Figure 2:
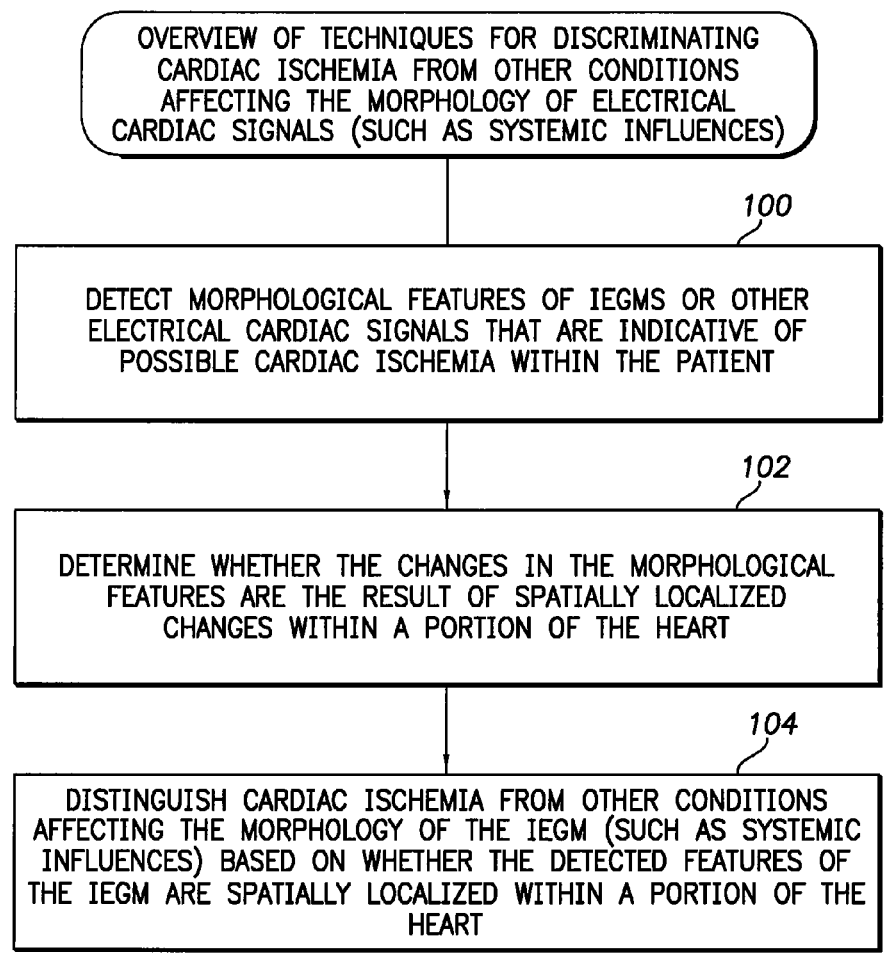
FIG. 2 is a flow diagram providing an overview of techniques that may be performed by the system of FIG. 1 for discriminating cardiac ischemia from other conditions affecting the morphology of electrical cardiac signals (such as hypo/hyperglycemia or other systemic influences) based on spatial localization of changes in IEGM signal morphology.
Figure 3:
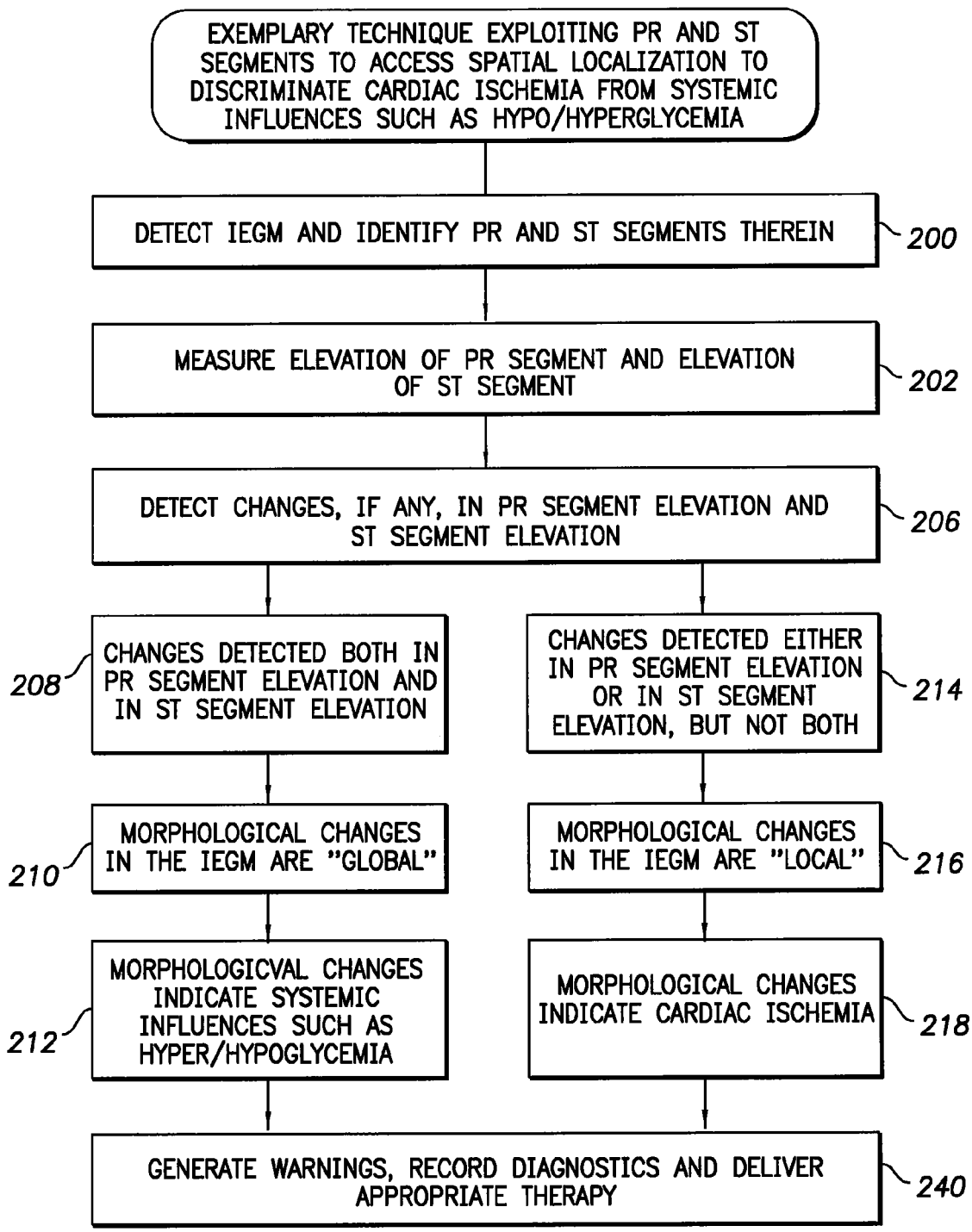
FIG. 3 is a flow diagram illustrating a first exemplary discrimination technique performed in accordance with the general technique of FIG. 2 that exploits PR and ST segments to access spatial localization to discriminate cardiac ischemia from systemic influences such as hypo/hyperglycemia.
Figure 4:
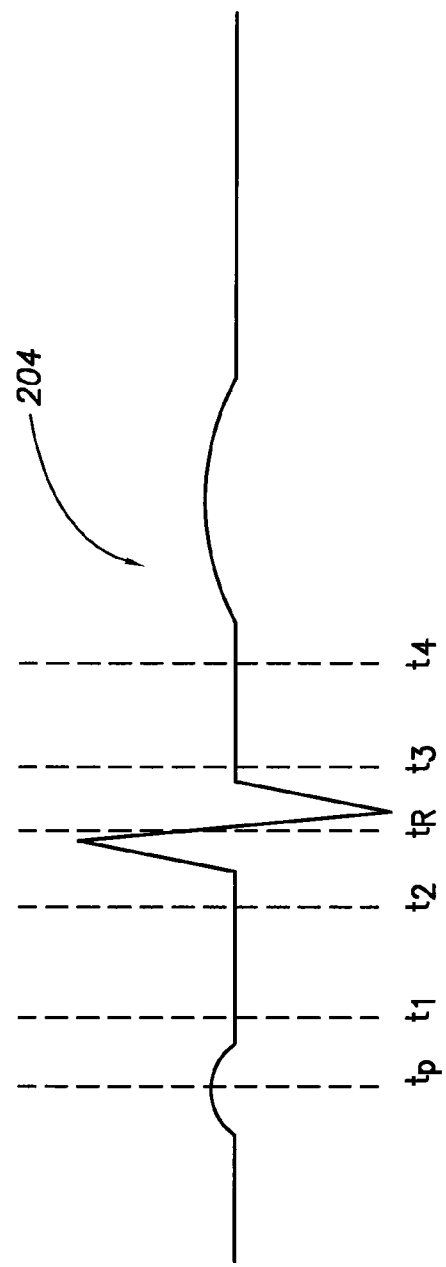
FIG. 4 is a stylized graph illustrating an exemplary IEGM and particularly identifying timing points therein used by the exemplary technique of FIG. 2 to identify PR and ST segments.

FIG. 2 summarizes the spatial localization-based ischemia detection and discrimination technique performed by the system of FIG. 1. Briefly, at step 100 of FIG. 2, the pacer/ICD detects morphological features of IEGMs or other electrical cardiac signals that are indicative of possible cardiac ischemia within the patient. In examples described below, PR and ST segment elevations are detected. However, other parameters indicative of ischemia may additionally or alternatively be detected, such as QTmax, QTend, Tend–Tmax intervals, etc. At step 102, the pacer/ICD then determines whether the changes in the morphological features are the result of spatially localized changes within a portion of the heart. In this regard, cardiac ischemia is classically associated with transient changes in electrogram amplitude during the ST segment. These changes are produced by electrophysiologic changes in the ischemic region of the heart to resting potential, amplitude of the plateau phase of the action potential, activation time (which affects conduction velocity), and/or the duration of the plateau phase of the action potential (which affects time to repolarization.) Systemic factors, though, can result in similar transient electrophysiologic effects that tend to confound attempts to detect ischemia. These systemic factors include hyper/hypoglycemia, hyper/hypokalemia (i.e. abnormal levels of serum potassium), the action of antiarrhythmic drugs, electrolyte imbalances, central nervous system disorders (e.g. subarrachnoid hemorrhage) and even minor metabolic disturbances (e.g. hyperventilation). (Note also that hypokalemia may appear secondary to insulin-induced hypoglycemia. Hypokalemia is known to manifest electrophysiologically as an elevated ST segment and prolonged QT interval.) However, such systemic influences are "global." That is, the systemic influences tend to affect electrophysiologic properties of the entire heart, or at least of regions of the heart larger than those affected by ischemia.

Hence, ischemia represents a spatially localized influence on IEGM morphology, whereas systemic conditions such as hyper/hypoglycemia represent a global influence on IEGM morphology. Thus, cardiac ischemia is distinguishable from the foregoing systemic influences based on whether IEGM changes are global or localized. If local IEGM features change in several locations at once, this indicates that the changes are likely due to a systemic influence. If local IEGM features change at one location and not at others, this is indicative of a localized effect such as ischemia or infarction. Note that still other factors, such as a prior myocardial infarction (i.e. a severe ischemic attack cause myocardial tissue death) and bundle branch block (i.e. a disruption in the normal flow of electrical pulses that drive the heart beat), can also affect IEGM morphology. However, these factors yield steady-state electrophysiologic changes relative to normal electrophysiology. Hence, a technique that relies on spatially-localized changes to IEGM morphology will not be unduly affected by a prior infarction or bundle branch block, as these conditions do not result in further on-going changes to the IEGM. The occurrence of a new infarction, of course, might cause changes to the IEGM that are confounding to the spatial localization-based discrimination techniques of FIG. 1. However, the patient will likely be acutely aware of the infarction due to the resulting pain and will immediately visit an emergency room or otherwise consult a physician and hence any warnings pertaining to ischemia, hypo/hyperglycemia, etc., would be unnecessary. Note also that an asymptomatic BBB or asymptomatic infarct might cause changes in IEGM morphology that might prevent the spatial localization-based discrimination technique from automatically detecting an ischemia. Hence, the ischemia detection technique is not infallible, but advantageous nonetheless.

Various exemplary techniques for use at step 102 to determine whether observed changes in morphological features of an IEGM are the result of spatially localized changes within a portion of the heart are described in detail below.

At step 104, the pacer/ICD then distinguishes cardiac ischemia from other conditions affecting the morphology of electrical cardiac signals based on, at least in part, on whether the changes in the morphological features are the result of spatially localized changes in the heart. Various exemplary techniques for use at step 104 to distinguish cardiac ischemia from other conditions are also described below.

FIGS. 3-7 illustrate an exemplary technique where the pacer/ICD exploits changes in PR and ST segments of an IEGM to determine whether or not the electrophysiological changes within the heart are spatially localized. That is, the pacer/ICD localizes signals to the atrium or to the ventricle by virtue of when in the cardiac cycle changes to the IEGM occur. If a change occurs in features arising from the ventricles, this represents a local change indicative of ischemia. If a change occurs in features arising from both the atria and the ventricles, then this represents a global change indicative of a systemic influence. More specifically, beginning at step 200 of FIG. 3, the pacer/ICD detects an IEGM and identifies PR and ST segments therein then, at step 202, measures the elevations of the PR and ST segments relative to some baseline. PR and ST segment elevation or amplitude may be quantified by any of a variety of methods. One exemplary method includes the following steps:

1) Digitizing atrial and/or ventricular IEGMs.
2) Identifying points in time in the electrogram, $t_P$ and $t_R$ respectively, when P-waves and QRS complexes occur. See FIG. 4, which illustrates an exemplary IEGM 204. This can be done, for example, via threshold detection methods on separate atrial and ventricular sense amplifier channels as well understood in the art.
3) Integrating some number of samples within the PR segment between $t_P+t_1$ through $t_P+t_2$ in order to obtain a metric of PR segment elevation/amplitude, and integrating some number of samples within the ST segment between $t_R+t_3$ and $tR+t_4$ to obtain a metric of ST segment elevation/amplitude.

At step 206, the pacer/ICD then detects changes, if any, in PR segment elevation and ST segment elevation over time. For example, the device may maintain a running average of PR and QT segment elevations and then detect any change relative to that running average that exceeds a predetermined detection threshold. In any case, if significant changes are detected both in PR segment elevation and in ST segment elevation, step 208, then the pacer/ICD thereby determines that these morphological changes in the IEGM are "global," at step 210. Hence, the pacer/ICD further determines or concludes, at step 212, that the morphological changes are indicative of systemic influences, such as hypo/hyperglycemia, hypo/hyperkalemia, etc. In contrast, if significant changes are detected either in PR segment elevation or in ST segment elevation, but not both, then the pacer/ICD thereby determines, at step 214, that these morphological changes in the IEGM are "local," at step 216. Hence, the pacer/ICD further determines or concludes, at step 218, that the morphological changes are indicative of cardiac ischemia. While PR segment elevation may be measured using IEGMs from any electrode pair, in the preferred embodiment PR segment elevation is measured using unipolar or bipolar electrodes in the atrium. Exemplary morphological changes in the IEGM are illustrated in FIGS. 5-7.

Figures 1, 5:
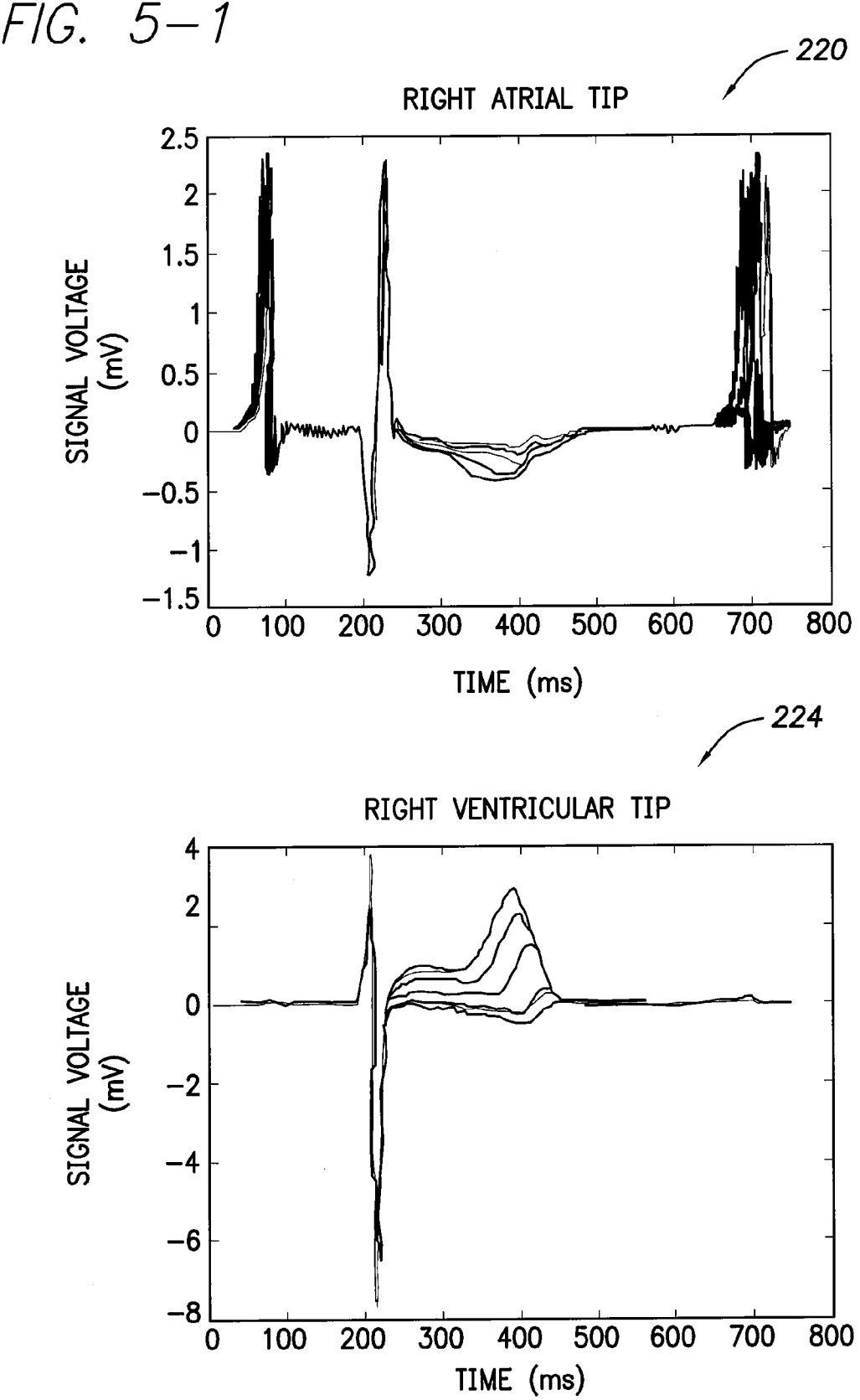
Figures 2, 5:
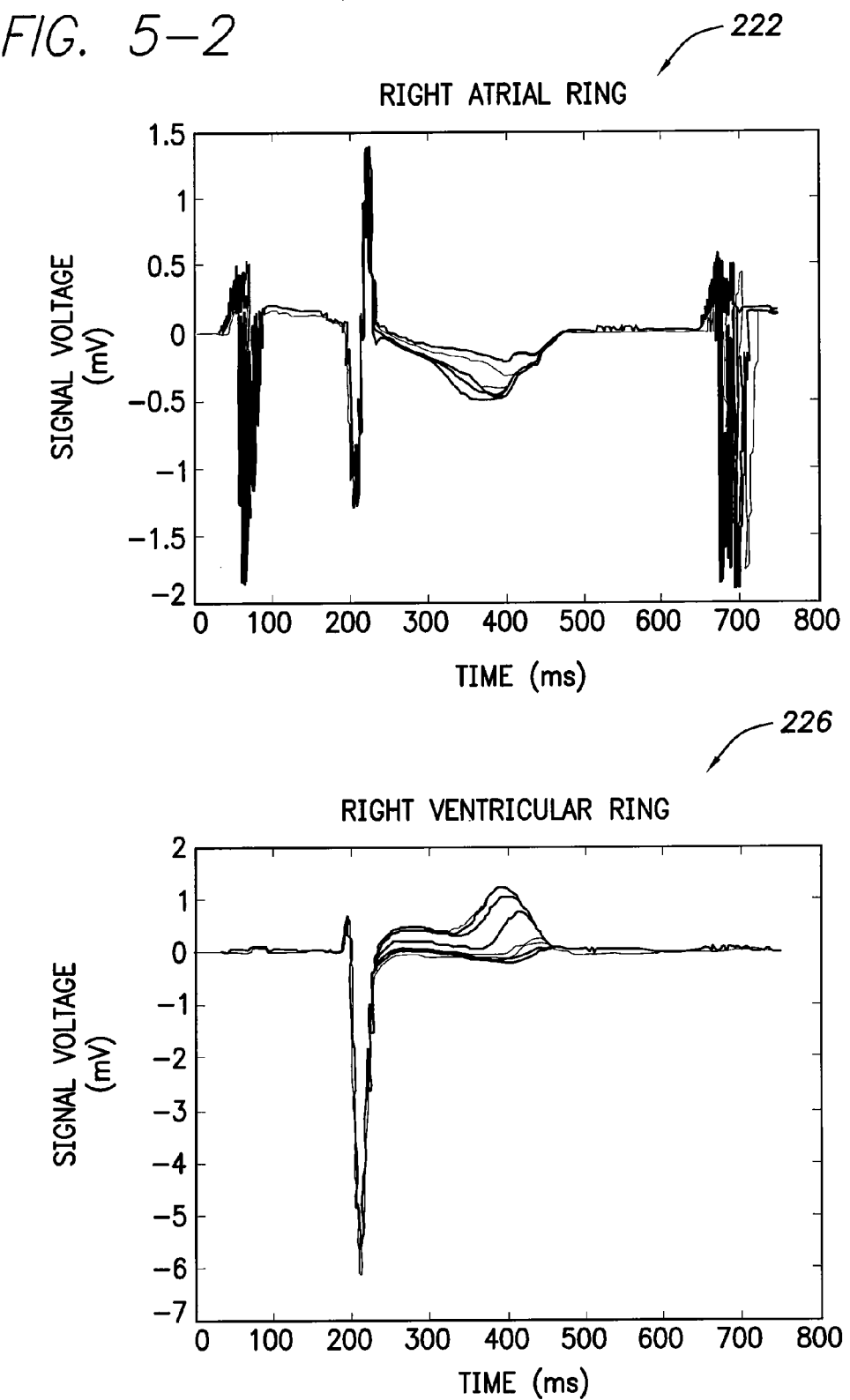

FIGS. 5-1 and 5-2 illustrate IEGM changes due to cardiac ischemia induced in the ventricles. The figures include IEGM traces obtained from four unipolar sensing configurations within an animal test subject. That is, a first set of IEGM traces 220 were obtained from a right atrial tip electrode via unipolar sensing. A second set of IEGM traces 222 were obtained from a RA ring electrode via unipolar sensing. A third set of IEGM traces 224 were obtained from a right ventricular (RV) tip electrode via unipolar sensing. A fourth set of IEGM traces 226 were obtained from a RV ring electrode via unipolar sensing. The vertical axis of the graph is signal voltage; the horizontal axis is time (in milliseconds) following a cardiac cycle starting point. In each graph, IEGM traces from numerous cardiac cycles are superimposed or overlaid over one another. The cardiac cycles were obtained over a period of time while cardiac ischemia was artificially induced within the test subject and hence changes over time in IEGM morphology caused by the onset of cardiac ischemia can be seen by comparing the overlaid traces. In each trace, the P-wave of each cycle occurs earliest in time and is then followed by the QRS complex, the T-wave, and the P-wave from the subsequent complex. (Note that the P-waves are very more prominent in the atrial unipolar traces but quite minimal in the ventricular unipolar traces.) It is readily apparent that changes in ST segment elevation (as well as T-wave morphology) are visible in all four sets of unipolar traces. However, no significant change in PR segment elevation is observed, even in the atrial unipolar traces where the P-waves are prominent. That is, as cardiac ischemia was induced within the test subject, the ischemia caused significant changes in ST segment elevations, but not in PR segment elevations. Thus, the onset of ischemia caused significant changes only in ST segment elevations but not PR segment elevations permitting the pacer/ICD to properly identify the morphological changes in the IEGM as being local changes indicative of cardiac ischemia rather than some system influence.

Figure 6:
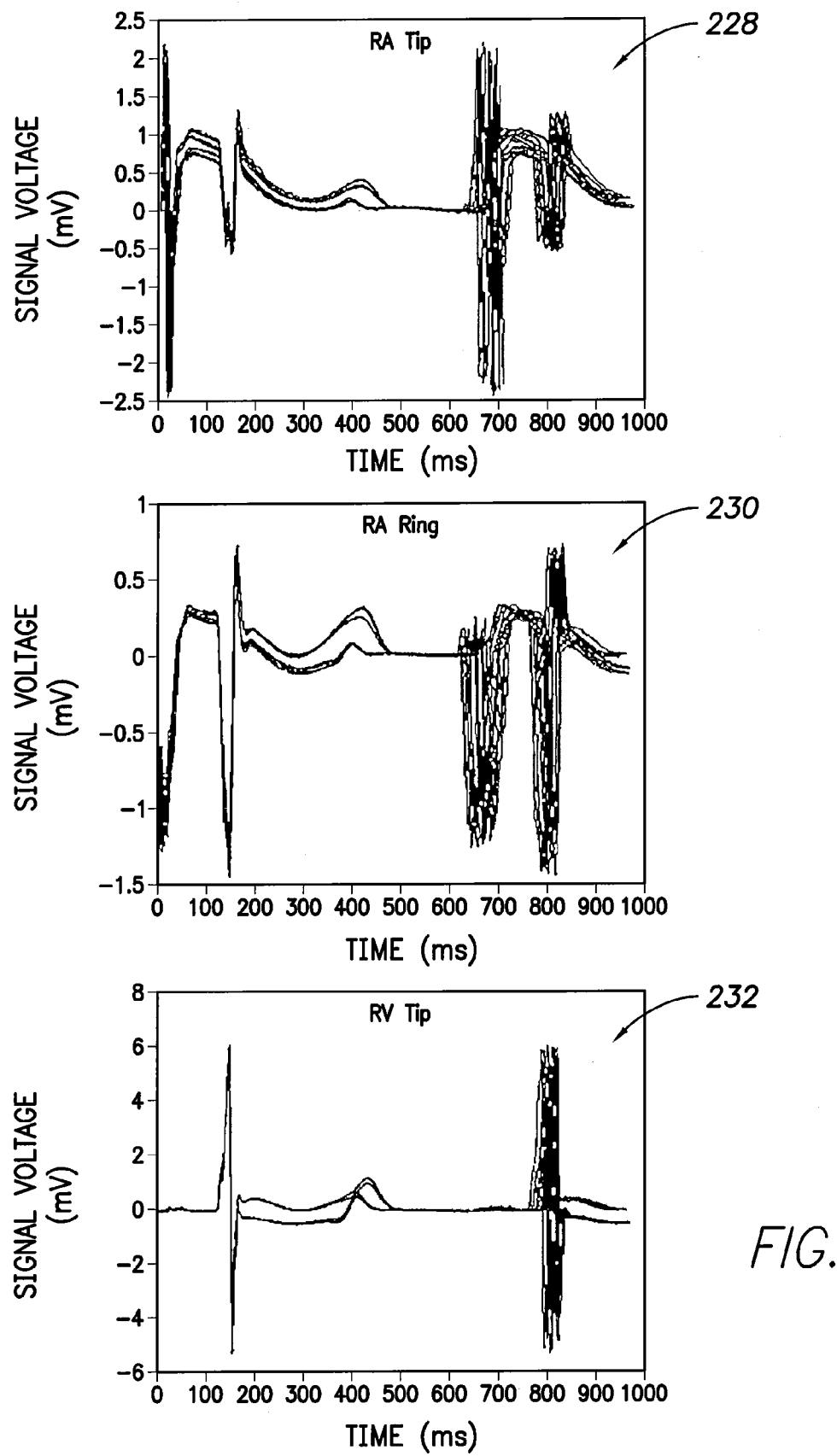
FIG. 6 sets forth exemplary IEGMs illustrating non-spatially localized variations in IEGMs due to hypoglycemia, and particularly illustrating the significant changes in both PR and ST segment elevations during hypoglycemia, which are exploited by the discrimination technique of FIG. 3.

FIG. 6 illustrates IEGM changes due to hypoglycemia. The figure includes IEGM traces obtained from three unipolar sensing configurations. That is, a first set of IEGM traces 228 were obtained from an RA tip electrode via unipolar sensing. A second set of IEGM traces 230 were obtained from a RA ring electrode via unipolar sensing. A third set of IEGM traces 232 were obtained from an RV tip electrode via unipolar sensing. Again, IEGM traces from numerous cardiac cycles are superimposed or overlaid over one another with the P-wave of each cycle occurring earliest followed by the QRS complex, the T-wave, and then the P-wave from the subsequent complex. The cardiac cycles were obtained over a period of time as hypoglycemia was induced within the test subject and hence changes over time in IEGM morphology caused by the onset of hypoglycemia can be seen by comparing the overlaid traces. It is readily apparent that changes in both PR segment elevation and ST segment elevation (as well as T-wave morphology) are visible in all three sets of unipolar traces. (Within graph 232, the changes to PR segment elevation are most easily seen in the end portion of the graph following the "subsequent" P-wave.) That is, as hypoglycemia was induced within the test subject, the hypoglycemia caused significant changes in both PR segment elevations and ST segment elevations. Thus, the onset of hypoglycemia caused significant changes in both PR segment elevations and ST segment elevations permitting the pacer/ICD to properly identify the morphological changes in the IEGM as being global changes indicative of a systemic influence rather than cardiac ischemia.

Figure 7:
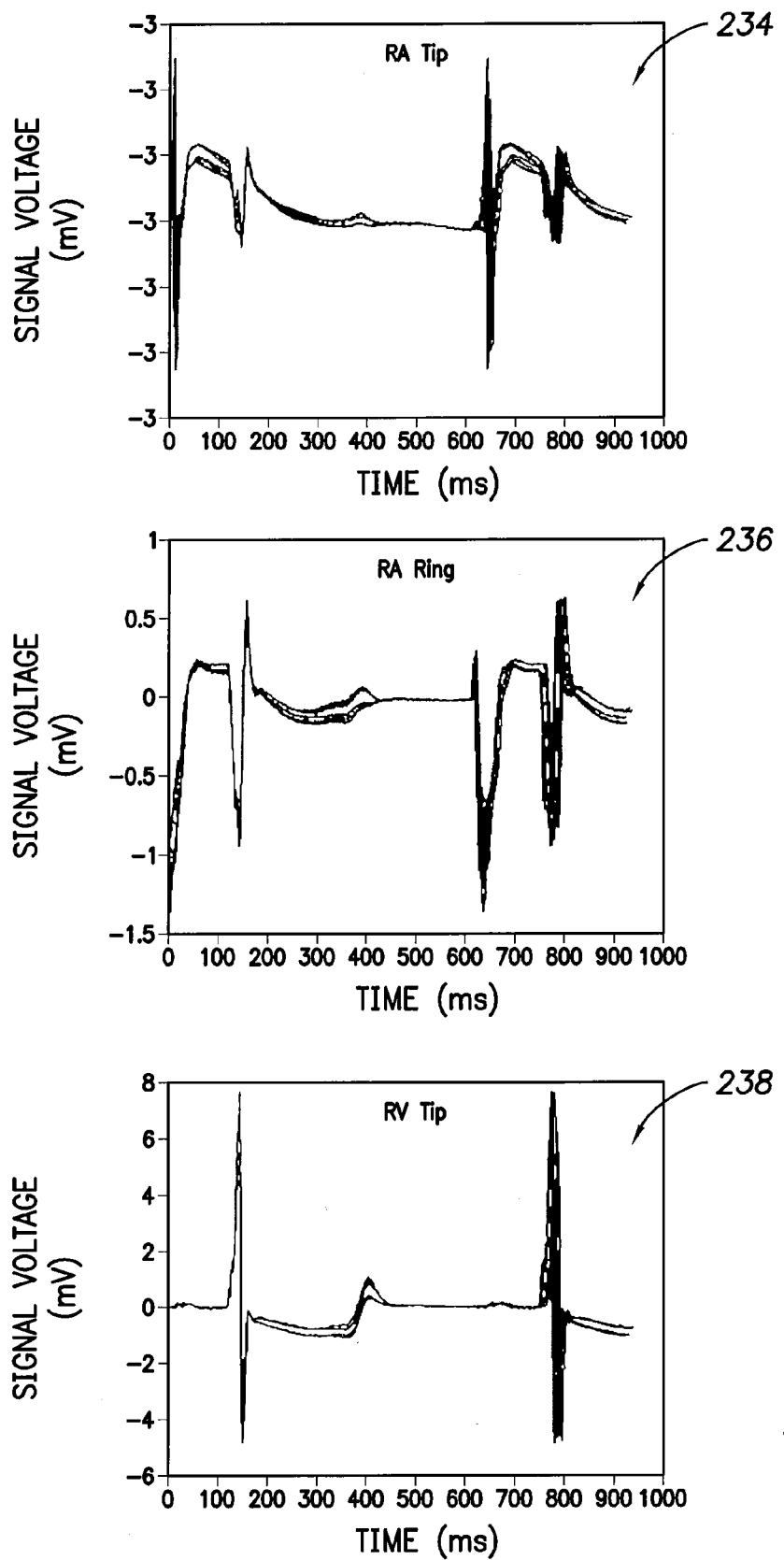
FIG. 7 sets forth exemplary IEGMs illustrating non-spatially localized variations in IEGMs due to hyperglycemia, and particularly illustrating the significant changes in both PR and ST segment elevations during hyperglycemia, which are exploited by the discrimination technique of FIG. 3.

FIG. 7 illustrates IEGM changes due to hyperglycemia. The figure includes IEGM traces 234, 236 and 238 obtained from the same three unipolar sensing configurations as in FIG. 6. Again, IEGM traces from numerous cardiac cycles are superimposed over one another with the P-wave of each cycle occurring earliest followed by the QRS complex, the T-wave, and then the P-wave from the subsequent complex. The cardiac cycles were obtained over a period of time as hyperglycemia was induced within the test subject thus allowing changes over time in IEGM morphology caused by the onset of hyperglycemia to be observed by comparing the overlaid traces. It is again readily apparent that changes in both PR segment elevation and ST segment elevation (as well as T-wave morphology) are visible in all three sets of unipolar traces. (Within graph 238, the changes to PR segment elevation are again most easily seen in the end portion of the graph following the "subsequent" P-wave.) Thus, the onset of hyperglycemia caused significant changes in both PR segment elevations and ST segment elevations permitting the pacer/ICD to properly identify the morphological changes in the IEGM as being global changes indicative of a systemic influence rather than cardiac ischemia.

Returning to FIG. 3, once the pacer/ICD has determined whether the cardiac ischemia has occurred, the device generates suitable warnings, records diagnostics and delivers appropriate therapy, at step 240. The particular warnings and therapy depend upon the programming and capabilities of the device. For example, in response to ischemia, the pacer/ICD may be programmed to (1) generate warnings; (2) adjust pacing therapy; (3) deactivate dynamic atrial overdrive (DAO) pacing (if it is currently being applied); (4) deliver anti-thrombolytics or other appropriate medications via a drug pump; (5) charge defibrillation capacitors (if the pacer/ICD is equipped to deliver defibrillation shocks). Adjustments to pacing therapy in response to cardiac ischemia may involve, for example, reduction of a base pacing rate so as to prevent a relatively high programmed base rate from exacerbating the ischemia. DAO is preferably deactivated, again to prevent exacerbation of the ischemia. DAO is described in U.S. Pat. No. 6,519,493 to Florio et al., entitled "Methods and Apparatus for Overdrive Pacing Heart Tissue Using an Implantable Cardiac Stimulation Device." Anti-thrombolytics or other medications are preferably delivered using an implanted drug pump, if one is provided. The aforementioned patent to Lord et al. also discusses implantable drug pumps. Routine experimentation may be employed to identify medications for treatment of cardiac ischemia that are safe and effective for use in connection with an implantable drug pump. Also, as before, diagnostics data is recorded for subsequent physician review. In some implementations, prior to delivering therapy or generating warnings, the pacer/ICD corroborates the detection of ischemia using other ischemia detection techniques. See, for example, the techniques discussed below that exploit changes in ST segment elevation and changes in the interval between Tmax and Tend. See, also, techniques described in the various patents and patent applications cited above, such as those to Ke et al., Min et al., Wang et al., Bharmi et al., and Fard et al.

Also, in some implementations, if the pacer/ICD determines that the condition affecting IEGM morphology is a systemic condition such as hypoglycemia or hyperglycemia, the device then determines the particular systemic condition and delivers therapy appropriate to that condition. Many of the patents and patent applications cited above provide techniques for detecting and distinguishing hyperglycemia and/or hypoglycemia or other systemic conditions such as hyperkalemia and/or hypokalemia. Techniques exploiting Tend–Tmax intervals are discussed below. Note that some cardioactive drugs can have cardiographic effects. Techniques for detecting and discerning between electrocardiographic effects of cardioactive drugs are described in U.S. Pat. No. 7,142,911, to Boileau et al. Those techniques may be used to identify changes, if any, within cardiac signals caused by medications, such that those changes can then be taken into account when detecting and distinguishing ischemia, hypoglycemia, hyperglycemia and hyperkalemia.

Assuming that a systemic condition such as hypo/hyperglycemia has been detected, then the device may automatically initiate appropriate therapy. For example, if an insulin pump is implanted within a diabetic patient, the pump may be controlled to adjust the dosage of insulin in response to hypoglycemia. Techniques for controlling delivery of therapy in response to hypoglycemia are set forth in the Patent Application of Kroll, cited reference above. Information regarding implantable insulin pumps may be found in U.S. Pat. No. 4,731,051 to Fischell and in U.S. Pat. No. 4,947,845 to Davis. The drug pump may also be equipped to deliver suitable medications in response to hyperglycemia, hyperkalemia, hypokalemia, etc. Alternatively, the patient may be instructed via an external device to take appropriate medications based on the detected condition and/or to titrate any medications already being taken.

Figure 8:
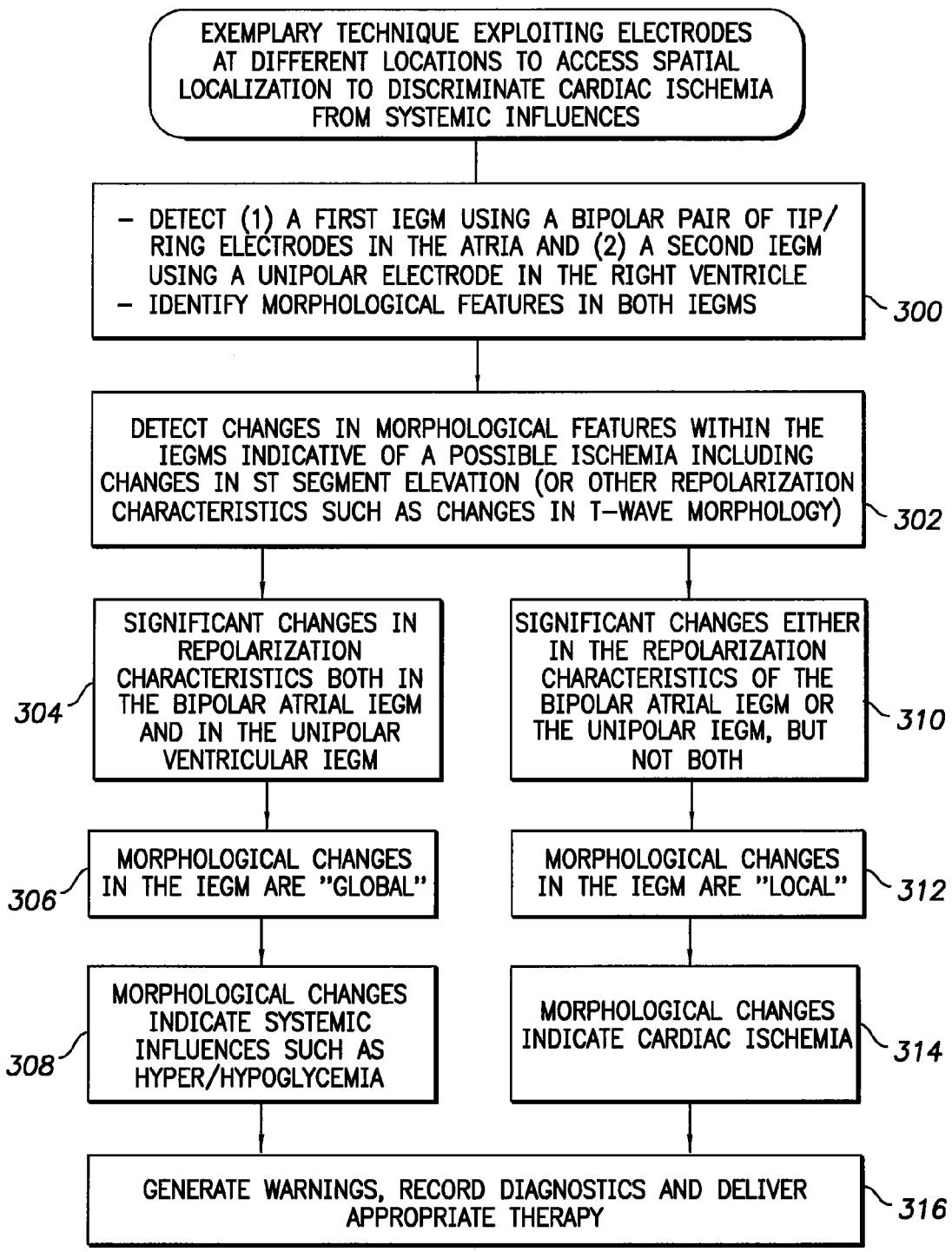
FIG. 8 is a flow diagram illustrating a second exemplary discrimination technique performed in accordance with the general technique of FIG. 2 that exploits a pair of cardiac signals to access spatial localization to discriminate cardiac ischemia from systemic influences.

FIG. 8 illustrates an exemplary spatial localization-based technique wherein the pacer/ICD instead exploits a pair of IEGM signals (one or more preferably derived bipolar electrodes) to access spatial localization to discriminate cardiac ischemia from systemic influences. Again, this is accomplished by deploying multiple electrodes at several locations within the heart (see FIG. 20, discussed below) at different various locations, e.g., the RA, the RV, the LV, the CS. In one example, at step 300, the pacer/ICD detects a (1) a first IEGM using a bipolar electrode in the atria and (2) a second IEGM using a unipolar electrode in the right ventricle. Also, at step 300, the pacer/ICD identifies morphological features in both IEGMs, such as ST segment elevations or T-wave morphology. At step 302, the pacer/ICD detects changes in the morphological features within the IEGMs indicative of a possible ischemia including changes in ST segment elevation (or other repolarization characteristics such as changes in T-wave morphology). At step 304, the device determines if significant changes in repolarization characteristics appear both in the atrial IEGM and in the ventricular IEGM. If so, then at step 306, the pacer/ICD thereby determines that these morphological changes in the IEGM are "global." Hence, the pacer/ICD further determines or concludes, at step 308, that the morphological changes are indicative of systemic influences, such as hypo/hyperglycemia, hypo/hyperkalemia, etc. In contrast, if significant changes in ST segment are observed either in the bipolar atrial IEGM or in the unipolar ventricular IEGM, but not both, at step 310, then the pacer/ICD thereby determines, at step 312, that these morphological changes in the IEGM are "local." Hence, the pacer/ICD further determines or concludes, at step 314, that the morphological changes are indicative of cardiac ischemia. At step 316, the device generates suitable warnings, records diagnostics and delivers appropriate therapy, which may include exploiting additional information to further specify any systemic conditions, e.g. hypo/hyperglycemia, etc.

Figure 9:
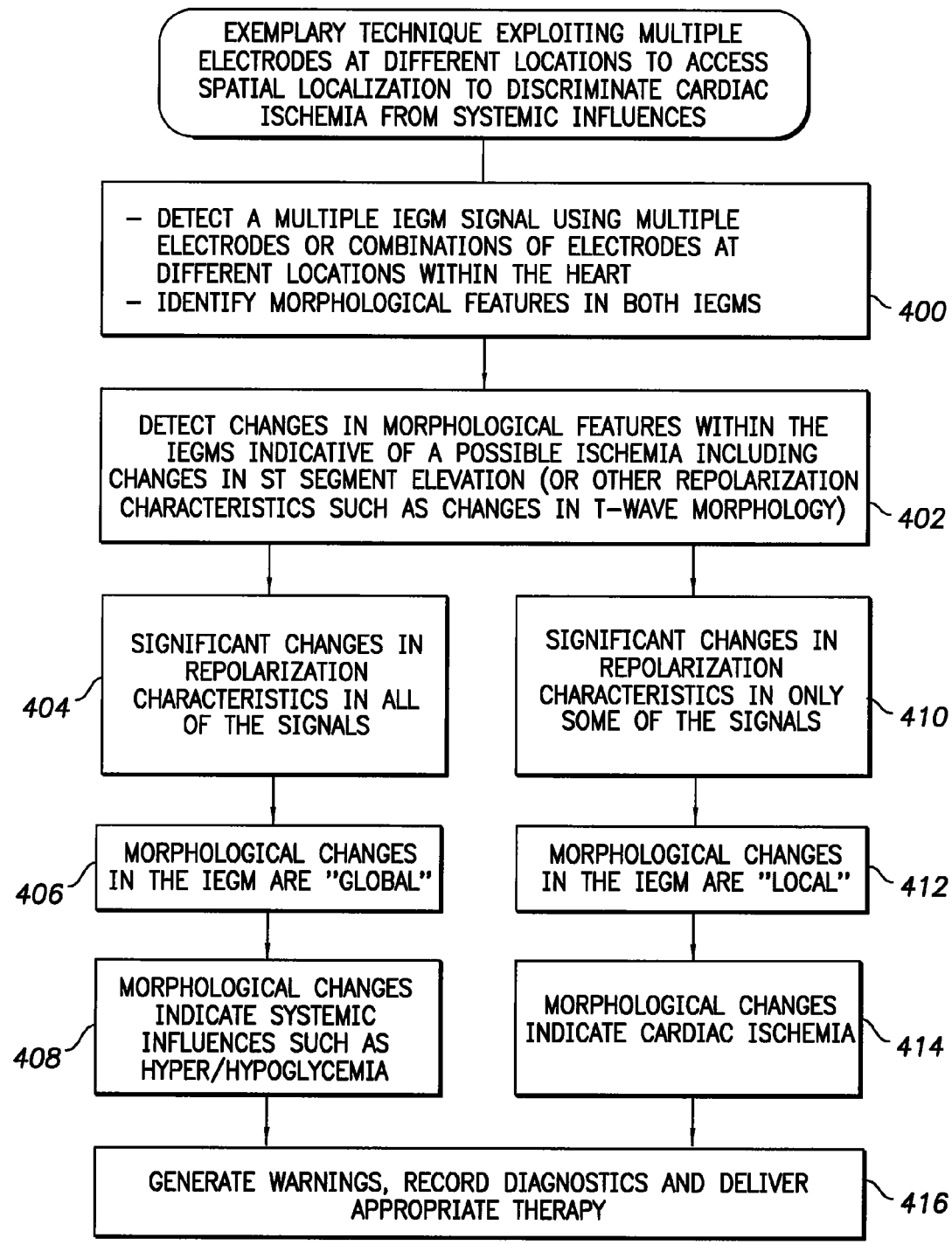
FIG. 9 is a flow diagram illustrating a third exemplary discrimination technique performed in accordance with the general technique of FIG. 2 that exploits multiple cardiac signals to access spatial localization to discriminate cardiac ischemia from systemic influences.

FIG. 9 illustrates an exemplary spatial localization-based technique wherein the pacer/ICD instead exploits multiple IEGM signals to access spatial localization to discriminate cardiac ischemia from systemic influences. Again, this is accomplished by deploying multiple electrodes at several locations within the heart (see FIG. 20, discussed below) at different various locations, e.g., the RA, the RV, the LV, the CS. In one example, at step 400, the pacer/ICD detects multiple IEGM signals using multiple electrodes or combinations of electrodes at different locations with the heart. Also, at step 400, the pacer/ICD identifies morphological features in the IEGMs, such as ST segment elevations or T-wave morphology. At step 402, the pacer/ICD detects changes in the morphological features within the IEGMs indicative of a possible ischemia including changes in ST segment elevation (or other repolarization characteristics such as changes in T-wave morphology). At step 404, the device determines if significant changes in repolarization characteristics appear all of the IEGM signals. If so, then at step 406, the pacer/ICD thereby determines that these morphological changes in the IEGM are "global." Hence, the pacer/ICD further determines or concludes, at step 408, that the morphological changes are indicative of systemic influences, such as hypo/hyperglycemia, hypo/hyperkalemia, etc. In contrast, if significant changes in repolarization characteristics are observed only in some of the IEGM signals, but not all, at step 410, then the pacer/ICD thereby determines, at step 412, that these morphological changes in the IEGM are "local." Hence, the pacer/ICD further determines or concludes, at step 414, that the morphological changes are indicative of cardiac ischemia. At step 416, the device generates suitable warnings, records diagnostics and delivers appropriate therapy, which may include exploiting additional information to further specify any systemic conditions, e.g. hypo/hyperglycemia, etc.

What have been described thus far are spatial localization-based techniques for distinguishing cardiac ischemia for systemic conditions. As can be appreciated, the various exemplary techniques set forth in FIGS. 3-9 can be combined to improve specificity. In the following section, repolarization interval-based techniques are discussed.

Overview of the Repolarization Interval-Based Detection Technique

Figure 10:
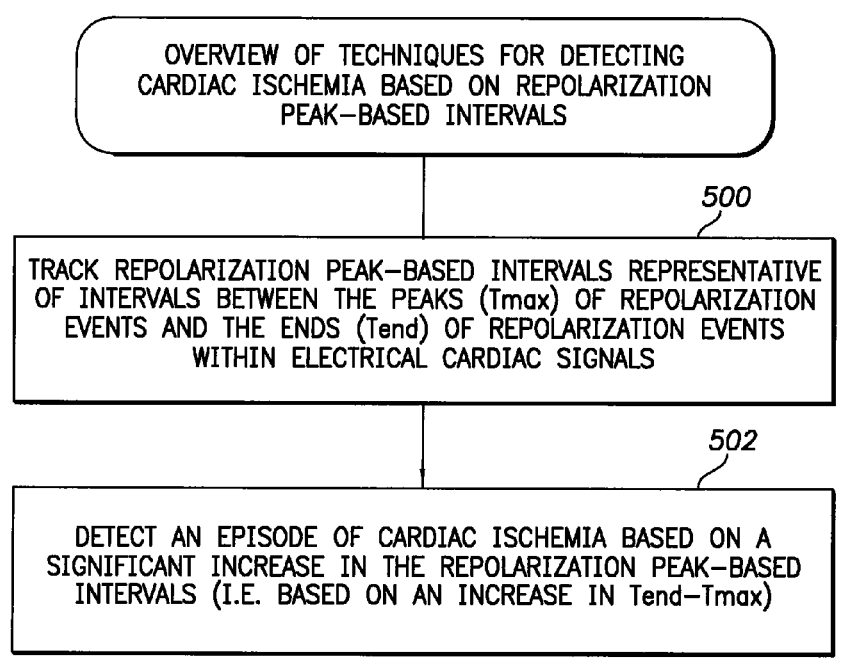
FIG. 10 is a flow diagram providing an overview of techniques that may be performed by the system of FIG. 1 for discriminating cardiac ischemia from other conditions affecting the morphology of electrical cardiac signals based on repolarization peak-based intervals within an IEGM signal.

FIG. 10 summarizes the repolarization-based ischemia detection and discrimination techniques performed by the system of FIG. 1. Briefly, at step 500 of FIG. 10, the pacer/ICD tracks repolarization peak-based intervals representative of intervals between the peaks (Tmax) of repolarization events and the ends (Tend) of the same repolarization events within IEGMs or other electrical cardiac signals. At step 502, the pacer/ICD then detects an episode of cardiac ischemia based, at least in part, on a significant increase in the repolarization peak-based intervals, i.e. based on an increase in Tend–Tmax (where Tend–Tmax represents the interval between Tend and Tmax.) In this regard, ischemia tends to shorten the action potential duration (APD) within the myocardium. However, this APD shortening occurs only in a localized ischemic region. Therefore, the ischemic region repolarizes early and the local T-wave for that region occurs early. Meanwhile the rest of the heart continues to repolarize at the normal time. The net effect is that the T-wave broadens, with the peak moving forward in time towards the R-wave. Since repolarization of normal tissue is not affected, and since ischemia only shortens APD, Tend does not change. Hence, Tend–Tmax becomes larger due to cardiac ischemia. (Note that a dispersion of refractoriness unmasked by catecholaminergic or autonomic influences may also cause a change in Tend–Tmax. In this regard, the literature identifies the dispersion of refractoriness, and the fact that it is different in diabetics compared to non-diabetics. However, the relative magnitude of change is presently not known. Nevertheless, changes due to hypoglycemia/ischemia are more acute than the chronic dispersion, hence enabling distinguishing between normal vs. hypoglycemia/ischemic conditions.)

One significant advantage in using the Tend–Tmax interval to detect an ischemic condition is that it is a relatively rate-independent parameter. The Q to Tend (QTend) or Q to Tmax (QTmax) intervals, discussed above, are rate-dependent, i.e., their values change with rate under normal conditions. However, Tend–Tmax does not change very much with rate under normal conditions. Therefore, Tend–Tmax does not require any significant rate correction (unlike QTmax or QTend intervals.) These issues will now be further discussed below with reference to various exemplary techniques provided in accordance with the general technique of FIG. 10.

Figure 11:
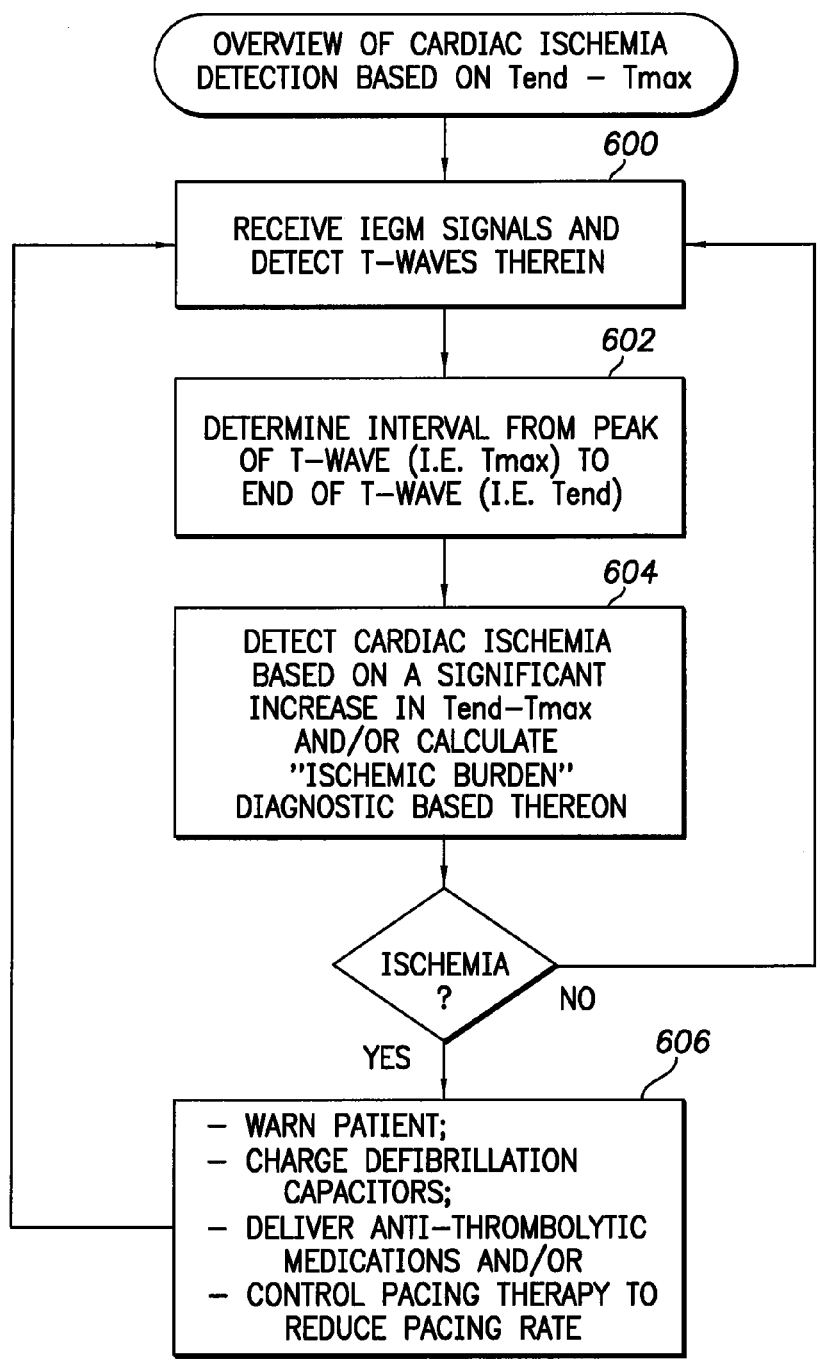
FIG. 11 is a flow diagram illustrating an exemplary repolarization-based discrimination technique performed in accordance with the general technique of FIG. 10 that exploits changes in Tend–Tmax intervals to detect cardiac ischemia.
Figure 12:
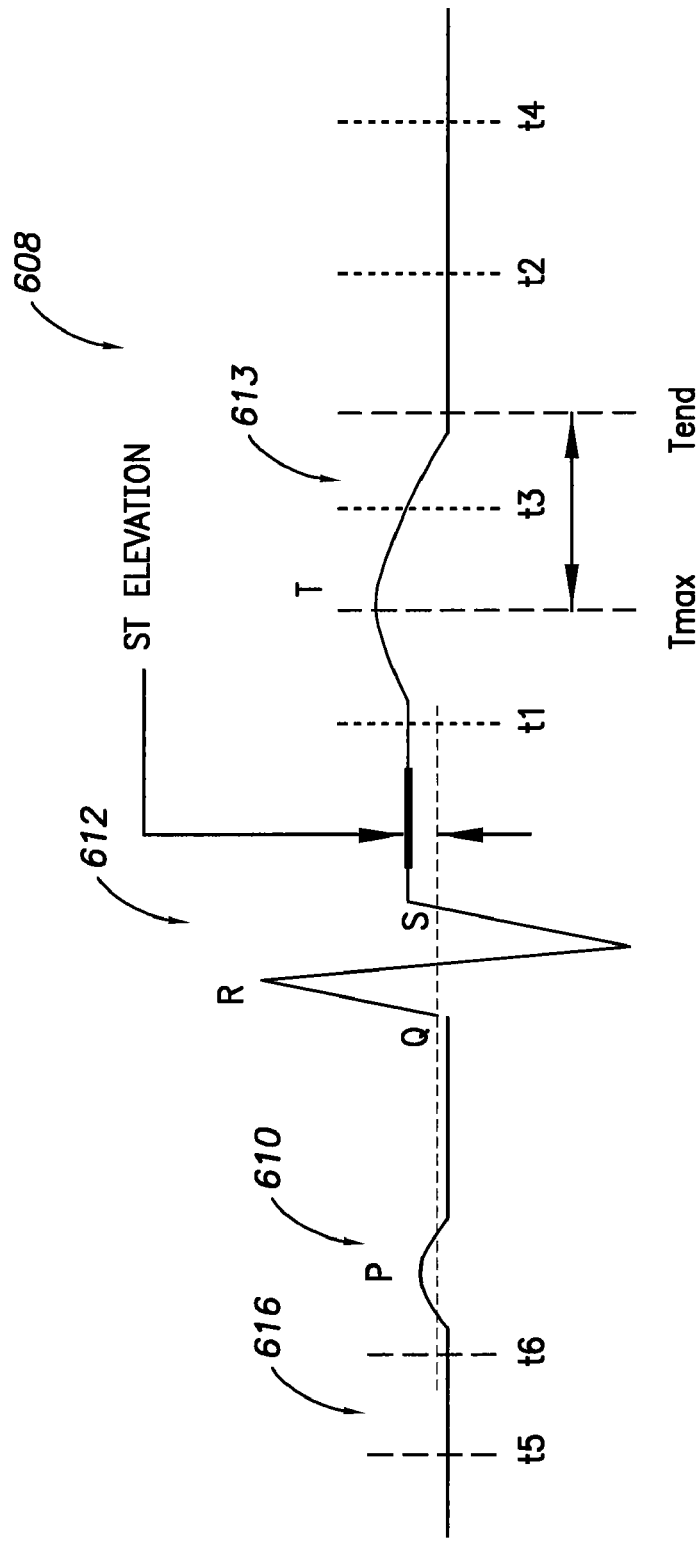
FIG. 12 is a stylized graph illustrating an exemplary IEGM and particularly identifying Tend–Tmax intervals used by the exemplary technique of FIG. 11.

FIG. 11 illustrates an exemplary implementation of a cardiac ischemia detection technique that exploits Tend–Tmax for use in accordance with the general technique of FIG. 12. Initially, at step 600, IEGM signals are received and T-waves are identified therein. Any of a variety of T-waves detection techniques may be exploited. Then, the interval from the peak of the T-wave (Tmax) to the end of the T-wave (Tend) is calculated, at step 602. As already noted, this interval is referred to herein as Tend–Tmax and the amount of change in the interval relative to some baseline value of the interval is ΔTend–Tmax. At step 604, the onset of a cardiac ischemia is detected based upon detection of a significant increase in Tend–Tmax. Routine experimentation may be performed to determine what constitutes "significant" insofar as changes in Tend–Tmax are concerned. In one example, a 10% or greater change in the parameter is deemed to be significant, i.e. if ΔTend–Tmax>10% of a baseline value of Tend–Tmax, then ischemia is indicated. Note that Tend–Tmax values may be derived from either paced or sensed events but values derived from paced and sensed events should not be combined. Additionally, or in the alternative, at step 604, the device calculates an "ischemic burden" based on Tend–Tmax or on ΔTend–Tmax, which is representative of the proportion of the time ischemia is detected. In one example, the ischemic burden is a numerical value representative of the extent to and/or the time during which Tend–Tmax is longer than its running average. Steps 600-604 are preferably performed periodically, such as once every 30 seconds. So long as no ischemia is detected, steps 600-604 are merely repeated. If ischemia is detected, however, the patient is warned, therapy is delivered, and/or other appropriate steps are taken at step 606, as already discussed above in connection with FIG. 3.

Hence, FIG. 11 illustrates one example of a technique that seeks to detect the onset of cardiac ischemia based primarily on changes in Tend–Tmax. Additional parameters of the IEGM signal, such as ST elevation, may be employed to confirm the detection made based upon to Tend–Tmax. Insofar as the detection of T-waves at step 600 is concerned, the invention may exploit techniques set forth in U.S. Patent Application Serial Number 2004/0077962 of Kroll, published Apr. 22, 2004, entitled "System and Method for Monitoring Blood Glucose Levels Using an Implantable Medical Device." Certain techniques described therein are particularly well suited for detecting T-waves with a high degree of accuracy to permit precise detection of features of the T-wave (such as its peak) so as to achieve more precise measurement of Tend–Tmax intervals. The invention also may exploit T-wave detection techniques set forth within the aforementioned patent application to Min et al., which help prevent P-waves from being misinterpreted as T-waves on unipolar sensing channels.

FIG. 12 illustrates the Tend–Tmax interval. Briefly, the figure provides a stylized representation of an exemplary IEGM trace 608 for a single heartbeat for a patient. The heartbeat includes a P-wave 610 representative of an atrial depolarization, a QRS complex 612 representative of a ventricular depolarization and a T-wave 613 representative of ventricular repolarization. The QRS complex itself is defined by points Q, R, and S. Q represents the beginning of the complex; R represents the peak of the complex; and S represents the end of the complex. In the examples described and illustrated herein, the aforementioned Tend–Tmax interval is specified as the time interval from the peak or maximum amplitude point of T-wave to the end of the T-wave, as shown. That is, Tmax may be defined as the point of maximum absolute value of amplitude of the electrogram within the interval t1 to t2. Exemplary values of t1 and t2 are 200 ms and 400 ms after the Q-wave respectively. Tend may be defined as the time at which a tailing portion of the T wave touches the isoelectric baseline within the interval t3 to t4. Exemplary values of t3 and t4 are 250 ms and 450 ms after the Q-wave respectively. Alternately, t3 may be defined as equal to Tmax.

Also, note that, in the particular example of FIG. 12, the peak of the T-wave is positive, i.e. it is greater than a baseline voltage of the IEGM signal. This need not be the case. In other examples, the peak has a negative value with respect to a baseline of the IEGM signal. The polarity of the entire signal may also be reversed. Herein, the peak or maximum amplitude of T-wave refers to the peak or maximum of the absolute value of the difference between the T-wave voltage and the baseline voltage of the IEGM signal. The baseline voltage 616 may be measured during an interval just prior to the P-wave, as shown by interval t5-t6. The interval may be, for example, 50 milliseconds (ms) in duration, beginning 100 ms prior to the P-wave. Alternatively, the interval may be timed relative to the QRS complex. If timed relative to the QRS complex, the interval may commence 250 ms prior to the R wave of the QRS complex. Also alternatively, a single detection point may be used, rather than a detection interval. The ST segment of the cardiac cycle is also identified in the figure and will be discussed below in connection with exemplary techniques that exploit both Tend–Tmax and ST segment.

Figure 13:
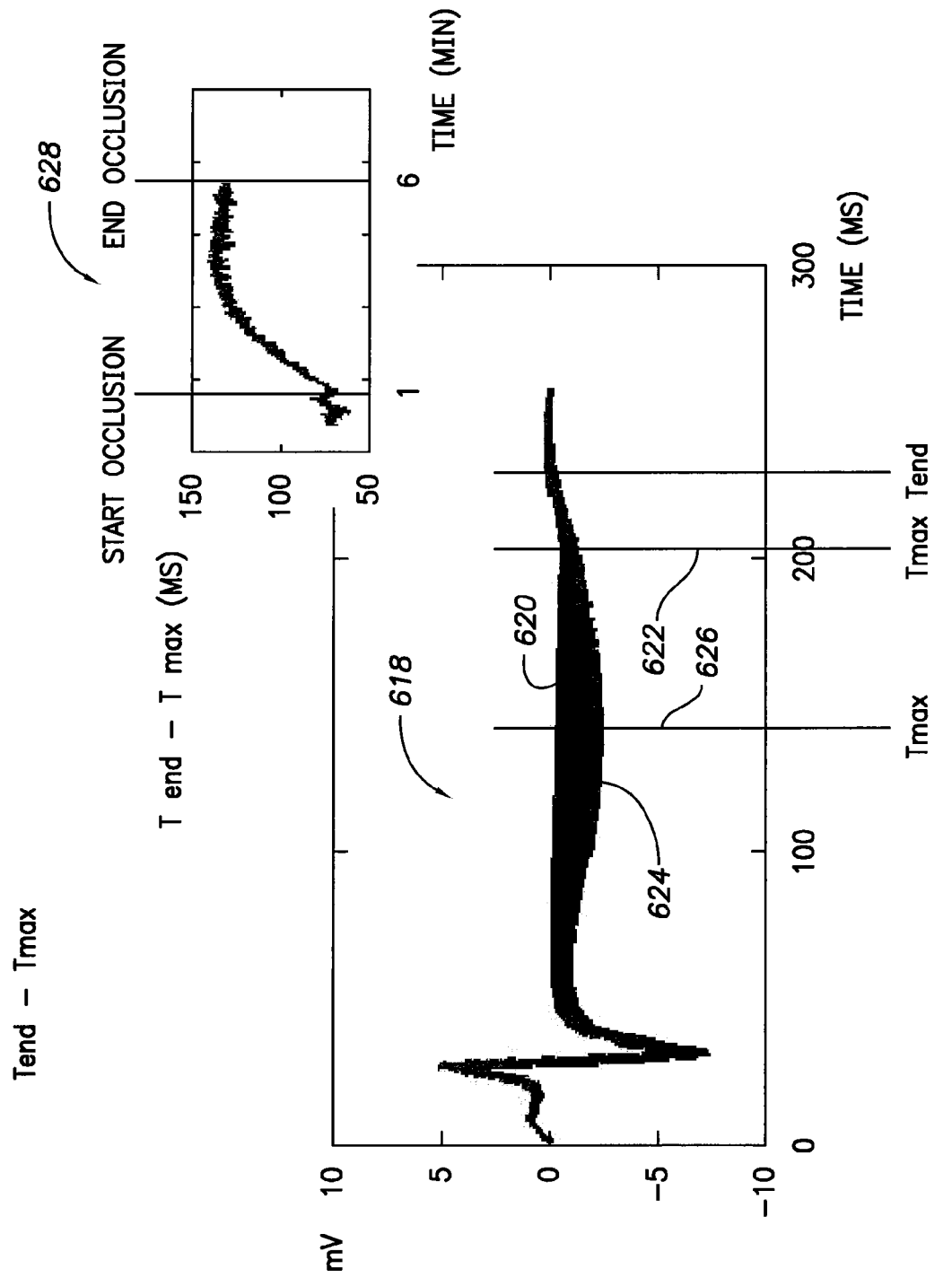
FIG. 13 sets forth exemplary IEGMs illustrating variations in IEGMs due to cardiac ischemia, and particularly illustrating significant changes in the duration of the Tend–Tmax interval during ischemia, which are exploited by the detection technique of FIG. 12.

FIG. 13 illustrates change in Tend–Tmax brought on by ischemia. A set of exemplary IEGM traces 618 were obtained from an animal test subject in which ischemia was induced by occluding the cardiac artery by balloon catheter. The traces of numerous cardiac cycles are superimposed over one another, illustrating changes in T-wave morphology as ischemia progressed within the test subject. Trace 620 was obtained before the artery was occluded and Tmax for that trace is identified by vertical line 622. Trace 624 was obtained several minutes after occlusion and Tmax for that trace is identified by vertical line 626. As can be seen Tmax line 626 occurs much earlier in the cardiac cycle than Tmax line 622, indicating movement of Tmax earlier in the cardiac cycle as ischemia worsens. However, there is little or no change in Tend. Hence, the Tend–Tmax interval increases during to ischemia. The upper right hand panel 628 illustrates the change in Tend–Tmax (in ms) as ischemia was induced, i.e. from the start of the occlusion to the end of the occlusion (when the balloon catheter was deflated). As can be seen, Tend–Tmax increases along with progression of ischemia. As noted above, this behavior of Tmax and Tend fits what is known about ischemia. In particular, that ischemia shortens the APD within a localized ischemic region in the heart causing the ischemic region to repolarize early while the rest of the heart continues to repolarize at the normal time. The net effect is that the T-wave broadens, with the peak moving earlier in the cardiac cycle, closer to the R-wave. Since repolarization of normal tissue is not affected, and since ischemia only shortens APD, Tend does not change significantly.

Note also that the IEGM traces 618 of the main graph exhibit a T-wave that is reversed in polarity with respect to stylized T-wave of the healthy patient represented in FIG. 12. T-wave inversion is typical during ischemia as well as during other conditions such as electrolyte abnormalities, which influence repolarization. Therefore, FIG. 13 illustrates that the Tend–Tmax indicator is valid even in the presence of a T-wave inversion. In any case, for the purposes of ischemia detection, the peak of the T-wave (whether positive or negative) moves forward toward the QRS-complex while the end of the T-wave is unaffected.

Thus, ΔTend–Tmax may be used to detect the onset of ischemia. Preferably, any change in Tend–Tmax from a current baseline value is tracked. In one example, the device tracks a running average of Tend–Tmax intervals (derived from sensed events) for use as a baseline value. A different baseline values may be calculated for paced beats. In any case, for each new heartbeat, the device compares the Tend–Tmax interval for that heartbeat against the appropriate baseline to calculate ΔTend–Tmax for that heartbeat. ΔTend–Tmax values are averaged over, e.g., eight to sixteen heartbeats and then compared against a predetermined Tend–Tmax-based ischemia detection threshold. If the average exceeds the threshold, cardiac ischemia is thereby indicated. The threshold is a programmable value set, for example, based upon a percentage of the running average of the Tend–Tmax interval. In one specific example, if ΔTend–Tmax is a positive value, which exceeds 10% of the running average of the Tend–Tmax intervals, cardiac ischemia is thereby indicated (i.e. Tend–Tmax has been found to be increased by 10%). Otherwise conventional threshold comparison techniques may be employed for use with ΔTend–Tmax. In another example, rather than comparing an average based on eight to sixteen values to the threshold, the occurrence of only a single ΔTend–Tmax value exceeding the threshold is indicative of ischemia. In yet another example, if ΔTend–Tmax exceeds the threshold for three out of five heartbeats, ischemia is indicated. Multiple thresholds may be defined, if desired, to trigger warning signals indicative of different levels of urgency. For example, if ΔTend–Tmax exceeds a first, lower threshold, a warning signal indicative of a moderate ischemia is issued. If ΔTend–Tmax exceeds a higher threshold, a second warning signal indicative of a more serious ischemia is issued. As can be appreciated, a wide variety of specific implementations maybe provided in accordance with the general techniques described herein. Routine experimentation may be performed to determine appropriate threshold levels.

Figure 14:
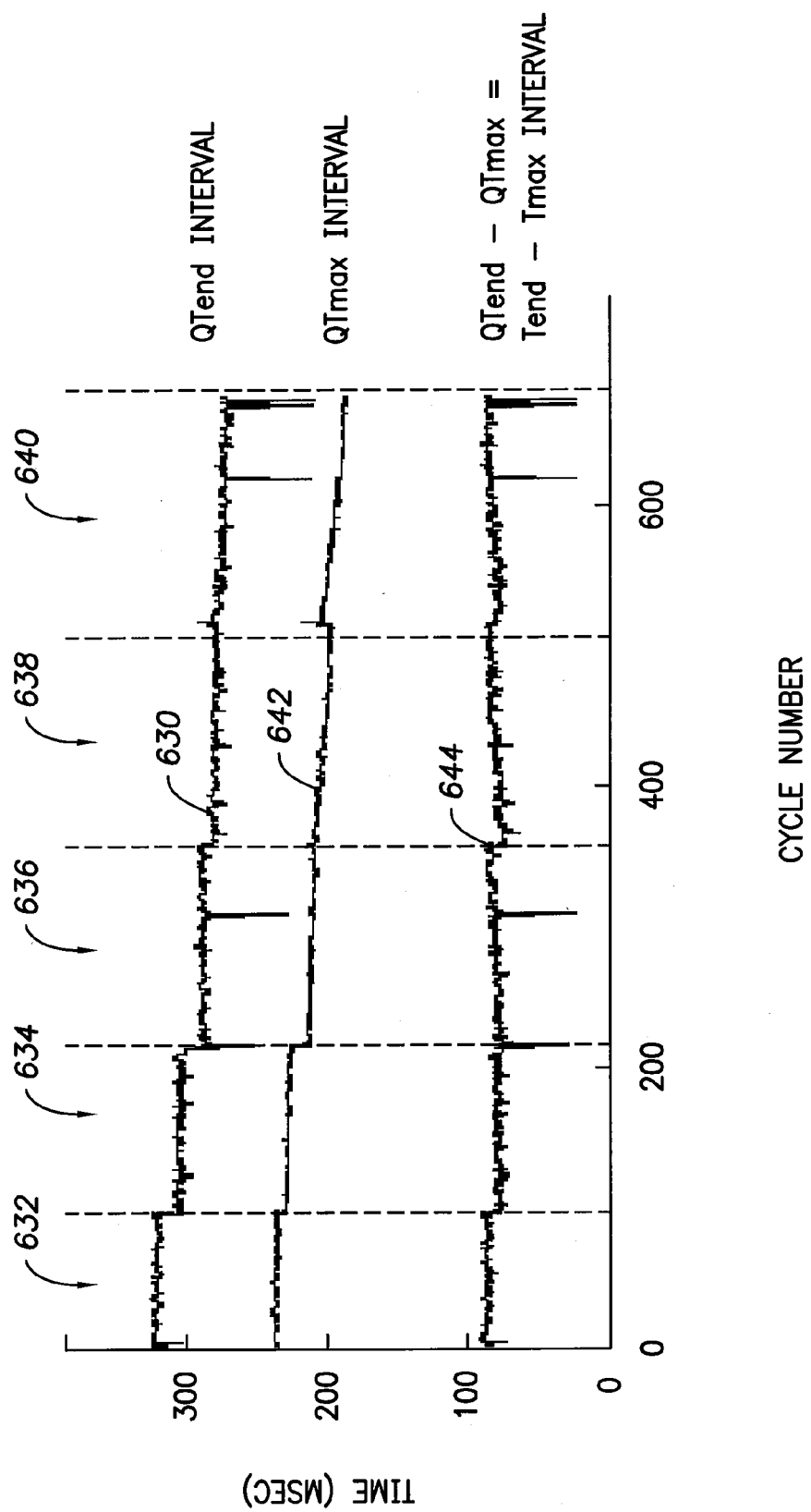
FIG. 14 illustrates the heart-rate independence of the Tend–Tmax parameter.

As noted, a significant advantage in using Tend–Tmax intervals to detect an ischemic condition is that it is a relatively rate-independent parameter. The aforementioned QTend and QTmax intervals are rate-dependent, i.e., their values change with rate under normal conditions. This is illustrated in FIG. 14. A set of QTend values are illustrated by way of graph 630 wherein the pacing rate was periodically increased. During a first interval 632, the pacing rate was 101 beats per minute (bpm). During a second interval 634, the pacing rate was 120 bpm. During a third interval 636, the pacing rate was 140 bpm. During a fourth interval 638, the pacing rate was 160 bpm. Finally, during a fifth interval 640, the pacing rate was 178 bpm. As can be seen, the QTend interval decreased significantly as the pacing rate increased, thus indicating that normalization is required before using the interval to detect ischemia (or other conditions.) Likewise, QTmax intervals, indicated by way of graph 642, also decreased, with increasing pacing rates. However, the Tend–Tmax intervals, indicated by way of graph 644, did not significantly change as the pacing rate changed, indicating that rate based normalization is not required. Note that no ischemia or other medical conditions were induced during the time intervals illustrated. Occasional spikes appearing in the data are indicative of noise or other anomalous data points. Note also that the Tend–Tmax interval can also be obtained by measuring QTend and QTmax and subtracting one from the other. That is, in systems already equipped to measure QTend and QTmax, Tend–Tmax can be obtained merely via subtraction. Moreover, although QTend and QTmax are affected by heart rate, their difference (Tend–Tmax) is not significantly affected.

Figure 15:
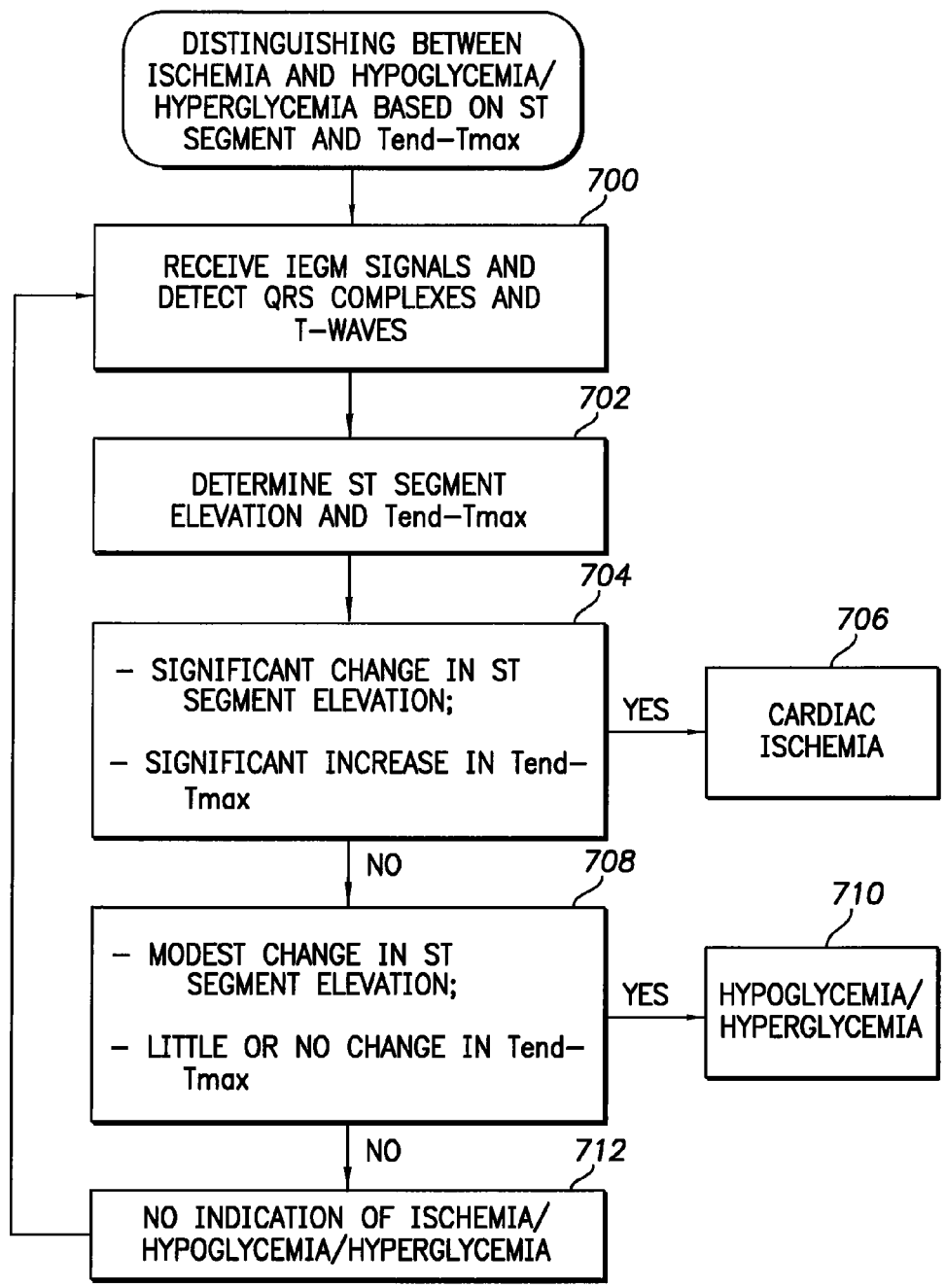
FIG. 15 is another flow diagram illustrating an exemplary repolarization-based discrimination technique performed in accordance with the general technique of FIG. 10 that exploits changes in Tend–Tmax intervals and ST segment intervals to detect cardiac ischemia and to also distinguish hypo/hyperglycemia from normal conditions.

FIG. 15 illustrates an exemplary technique for distinguishing between cardiac ischemia and hypoglycemia/hyperglycemia wherein Tend–Tmax and deviations in ST segment elevation are both examined. Beginning at step 700, the implanted device receives IEGM signals and detect QRS complexes and T-waves. At step 702, the device determines or measures ST segment elevation and Tend–Tmax for each individual heartbeat (as derived from either sensed events only or paced events only). ST segment elevation is shown in FIG. 12. Based upon the measured values of Tend–Tmax and ST segment elevation, the device detects and distinguishes between cardiac ischemia and hypoglycemia/hyperglycemia. Briefly, at steps 704-706, the device detects cardiac ischemia based upon any relatively large change in ST segment elevation combined with a concurrent increase in Tend–Tmax. At step 708-710, the device detects hypoglycemia/hyperglycemia based upon a significant but more modest change in ST segment elevation combined with little or no change in Tend–Tmax. To distinguish a significant change in ST segment elevation from a modest one, the device may employ separate thresholds. The conditions set forth in the steps 704 and 708 are listed in Table I.

TABLE I

|  | ST Segment | Tend-Tmax |
| --- | --- | --- |
| Ischemia | Significant change | Significant Increase |
| Hypoglycemia/ Hyperglycemia | Modest change | Little or no change |

Appropriate warning signals are issued or therapy is delivered at steps 706 and 710 upon detection of ischemia or hypoglycemia/hyperglycemia, respectively. If neither of the conditions set forth in steps 704 and 708 are met, then no indication of ischemia or hypoglycemia/hyperglycemia is made, step 712, and processing instead returns to step 704 for examination of additional IEGM signals. By examining both ST segment elevation and Tend–Tmax, a greater degree of reliability and specificity is achieved. Additional detection parameters may be examined as well to improve specificity, including QTmax and QTend intervals (properly normalized) and/or including otherwise conventional detection parameters and/or the parameters set forth in the aforementioned patent applications to Wang et al. and Min et al. and in the techniques of U.S. Pat. Nos. 7,272,436 and 7,297,114, cited above.

Figure 16:
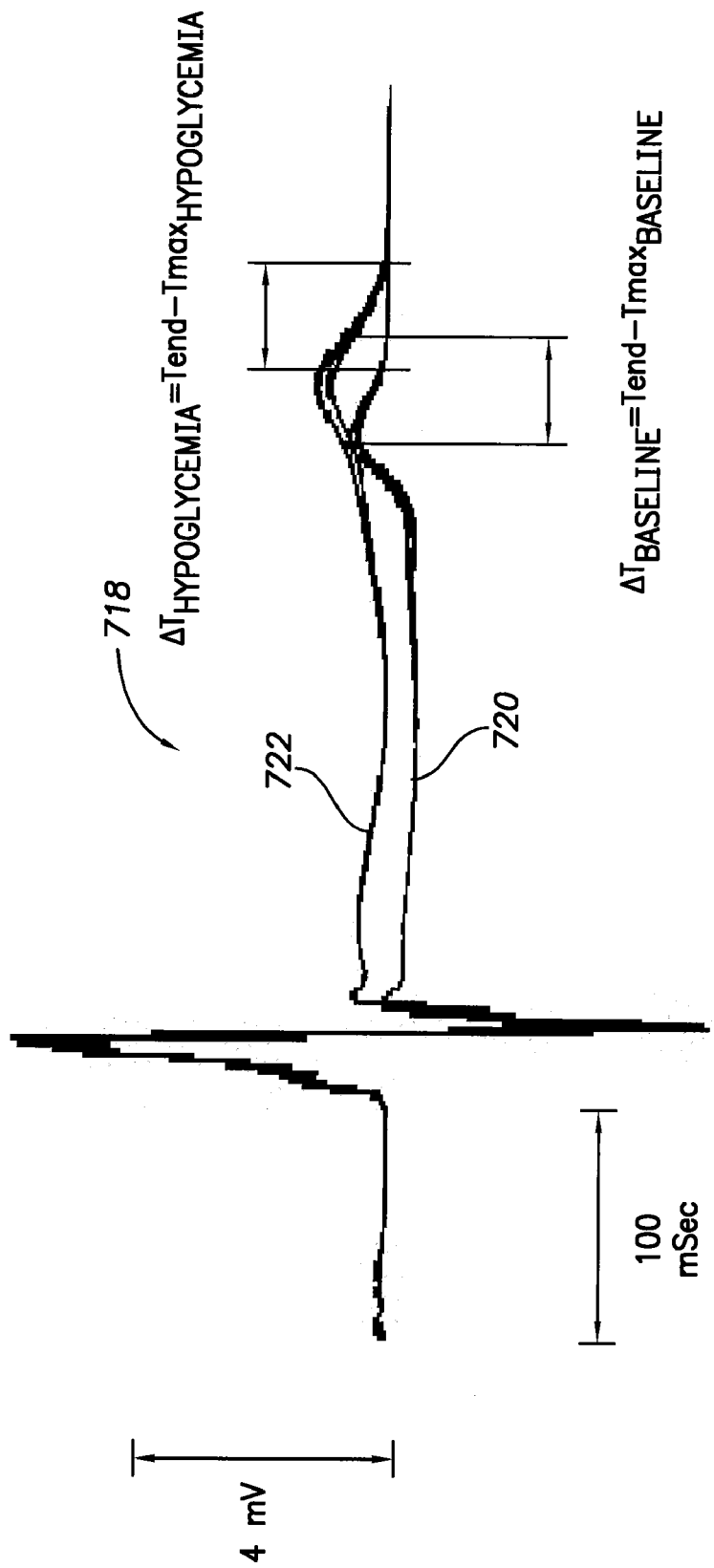
FIG. 16 sets forth exemplary IEGMs illustrating variations in IEGMs due to hypoglycemia, and particularly illustrating the lack of any significant changes in the duration of the Tend–Tmax interval during hypoglycemia, which are exploited by the discrimination technique of FIG. 15.
Figure 17:
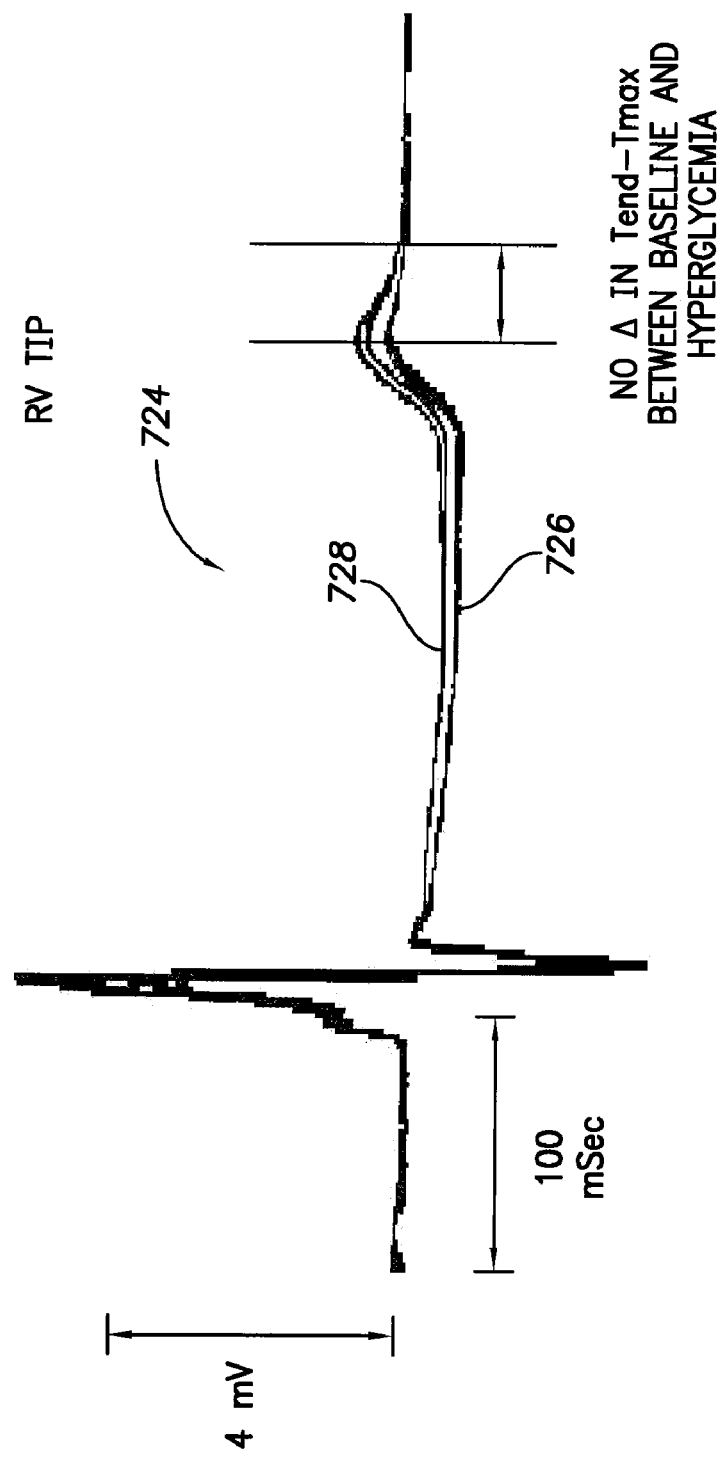
FIG. 17 sets forth exemplary IEGMs illustrating variations in IEGMs due to hyperglycemia, and particularly illustrating the lack of any significant changes in the duration of the Tend–Tmax interval during hyperglycemia, which are exploited by the discrimination technique of FIG. 15.

FIGS. 16 and 17 illustrate the influence on IEGM morphology due to hypoglycemia and hyperglycemia, respectively. FIG. 16 illustrates a set of IEGM traces 718 (RVT to case) superimposed one another, both during normal conditions and insulin-induced hypoglycemia. As can be seen, the Tend–Tmax interval in hypoglycemia remains relatively unchanged from baseline 720 to hypoglycemic 722. This is because hypoglycemia (or hypokalemia occurring secondary to hypoglycemia) causes Tmax and Tend to change together. Note also that a relatively modest change in ST segment elevation is also observed during hyper/hypoglycemia, in contrast to the more significant changes in ST segment elevation observed during ischemia (FIG. 13.) FIG. 17 illustrates a set of IEGM traces 724 (also RVT to case) superimposed one another, both during normal conditions and insulin-induced hyperglycemia. As can be seen, the Tend–Tmax interval in hyperglycemia remains relatively unchanged from baseline 726 to hyperglycemic 728. But in this case, Tend–Tmax interval did not change because both Tend and Tmax did not change in response to the hyperglycemic conditions (rather than both changing as with hypoglycemia). Note also that a relatively modest change in ST segment elevation is also observed during hyperglycemia, again in contrast to the more significant changes in ST segment elevation observed during ischemia.

Thus FIGS. 15-17 illustrate that ST segment elevation may be used as additional parameter. ST segment elevation for a cardiac QRST complex may be measured as follows. The mean of a set of IEGM sample values taken during the ST segment is compared to the mean of a reference set of IEGM samples. The reference set of sample values may be defined as those samples occurring during a time window beginning at t5 prior to the P-wave and ending at t6 prior to the P-wave (FIG. 12). The ST segment sample set is preferably taken from some interval within the ST segment beginning after the end of the S-wave and ending before the start of the T-wave. With these intervals properly defined, the ST segment elevation is independent of changes in rate. Changes in ST segment elevation may be defined as the mean of the samples in the ST segment sample set less the mean of the samples in the reference set.

Note that variability may arise in the various measured parameters due to random processes and due to other processes independent of those the pacer/ICD is quantifying. Various methods maybe employed to account for these variations. For example, the Tend–Tmax interval and ST elevation may be measured on an ensemble-average of several (e.g. 8-16) consecutive or approximately consecutive QRST complexes. Alternately, Tend–Tmax and ST elevation may be measured for each of several individual consecutive or approximately consecutive complexes and statistics calculated on the several measurements. Statistics to be calculated include the mean and the variance.

Note also that ST segment elevation is typically approximately equal to the isoelectric baseline (taken to be the pre-P value discussed earlier) in the absence of a pathological condition. Therefore, ST segment elevation may be taken as an absolute measurement at any time, and ischemia detected if the elevation of the ST segment exceeds a threshold. Likewise, Tend–Tmax is expected to remain approximately constant even under the influence of rate changes and other effects as described above. Therefore, Tend–Tmax may also be taken as an absolute measurement at any time, and ischemia detected if Tend–Tmax exceeds a threshold.

ST segment elevation and Tend–Tmax may also change slightly over time under normal circumstances. Such slow changes are typically due to systemic influences such as electrolyte imbalances. However changes in these parameters due to acute ischemia are expected to evolve rapidly (e.g. over the course of a minute or two), where changes due to systemic influences (e.g. hypokalemia) are expected to evolve more slowly. Therefore, it may be desirable to compare ST elevation and/or Tend–Tmax to one or more historical baselines on a periodic basis. A change in ST elevation relative to a historical baseline may be termed AST elevation. A change in Tend–Tmax relative to a historical baseline may be termed ΔTend–Tmax. Ischemia may be detected if AST elevation and/or ΔTend–Tmax exceed suitable thresholds.

The definition of "historical baseline" (not to be confused with isoelectric baseline) and the interval at which diagnoses are attempted may depend upon the application. In one example, ischemia burden is measured every hour for the purposes of a long-term diagnostic record. Tend–Tmax is measured every hour and compared to baseline values determined at a single point in time (e.g. at implant or at the command of a clinician) or to an average of values determined over a relatively long period of time (e.g. over the previous week) to determine ΔTend–Tmax. In the context of acute ischemia event detection, ΔTend–Tmax is measured relatively often (e.g. every 30 seconds). In this context, baseline is more appropriately determined from a relatively recent history (e.g., a moving average of values measured over the previous hour). Acute myocardial ischemia is indicated if ΔTend–Tmax measurements begin to exceed a threshold. In some examples, only one ΔTend–Tmax measurement must exceed the threshold. In other examples, several (e.g. three) consecutive measurements must exceed the threshold. In still other examples, the rate of measurements exceeding threshold must itself exceed a second threshold, e.g. at least 3 of 5 consecutive measurements. In other cases, a measure of statistical significance (e.g. T-statistic) between baseline and subsequent measurements must exceed a threshold. Note that Tend–Tmax and ST elevation measurements may be made on intrinsic or paced complexes, but paced and intrinsic measurements should not be combined.

Figure 18:
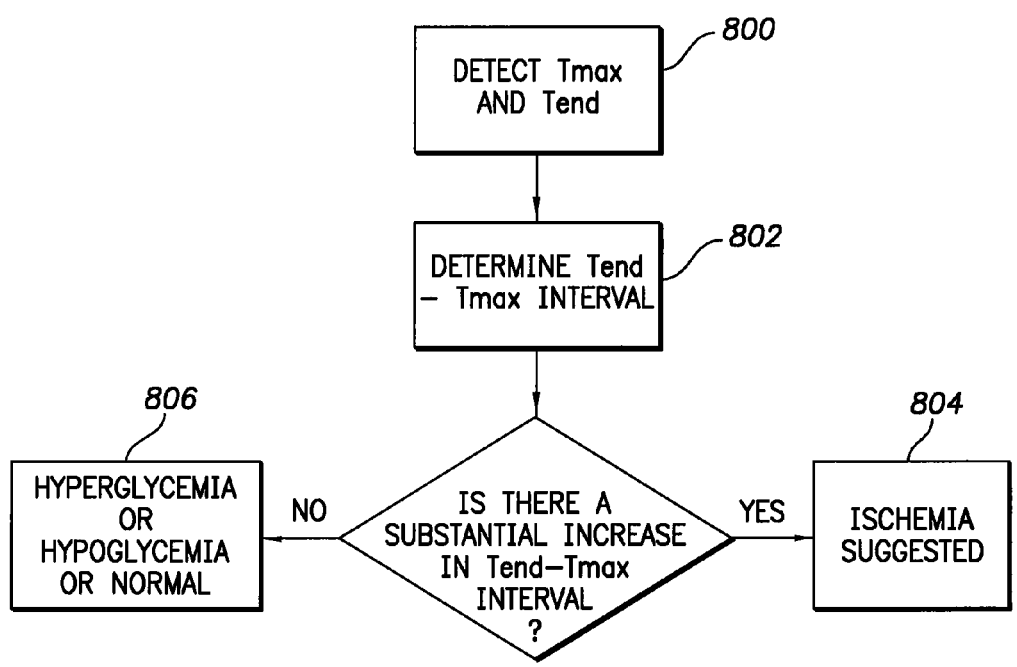
FIG. 18 is a flow diagram illustrating an exemplary repolarization-based discrimination technique performed in accordance with the general technique of FIG. 10 that exploits changes in Tend–Tmax intervals to detect cardiac ischemia.
Figure 19:
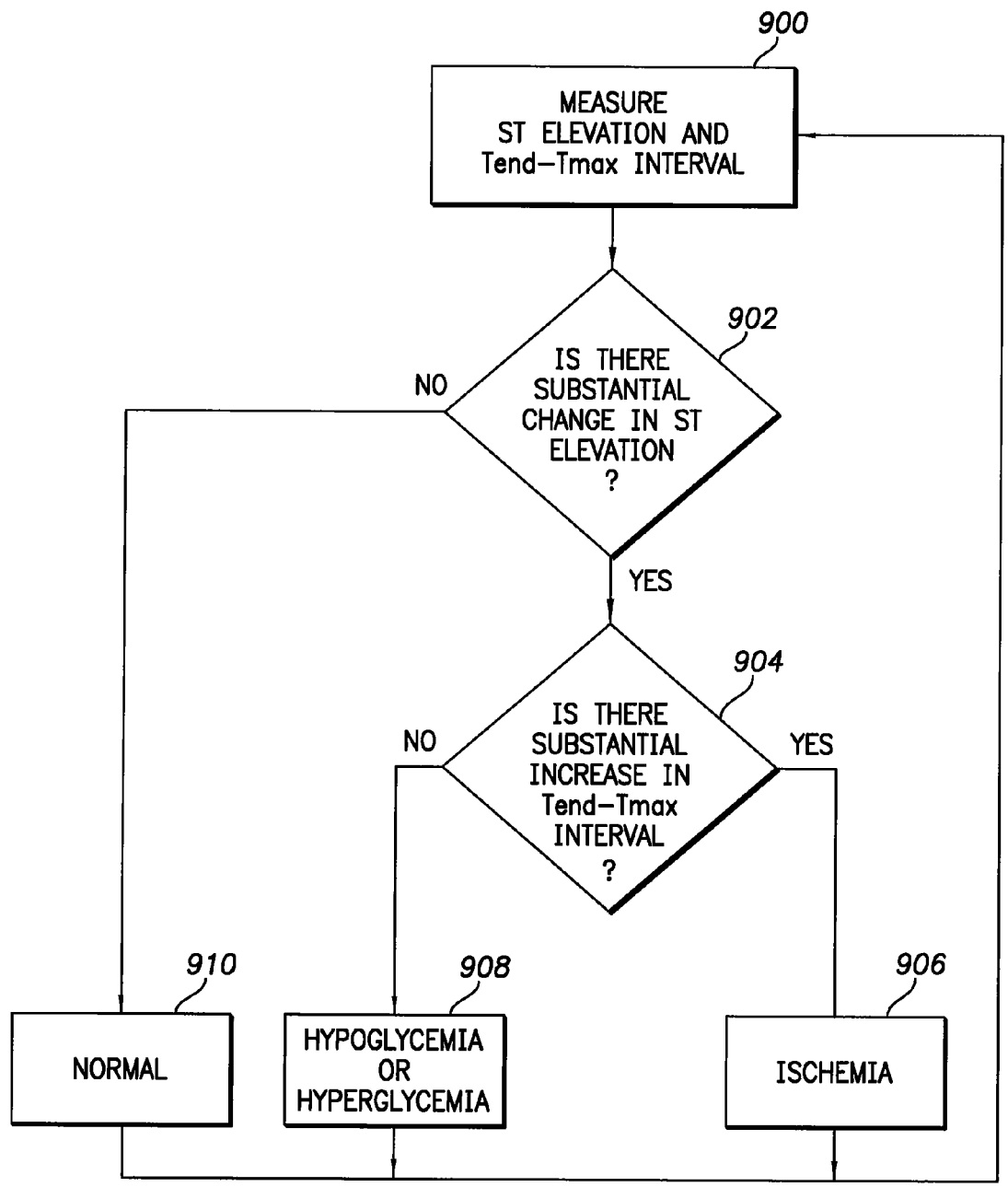
FIG. 19 is a flow diagram illustrating an exemplary repolarization-based discrimination technique performed in accordance with the general technique of FIG. 10 that exploits changes in Tend–Tmax intervals to detect cardiac ischemia.
Figure 20:
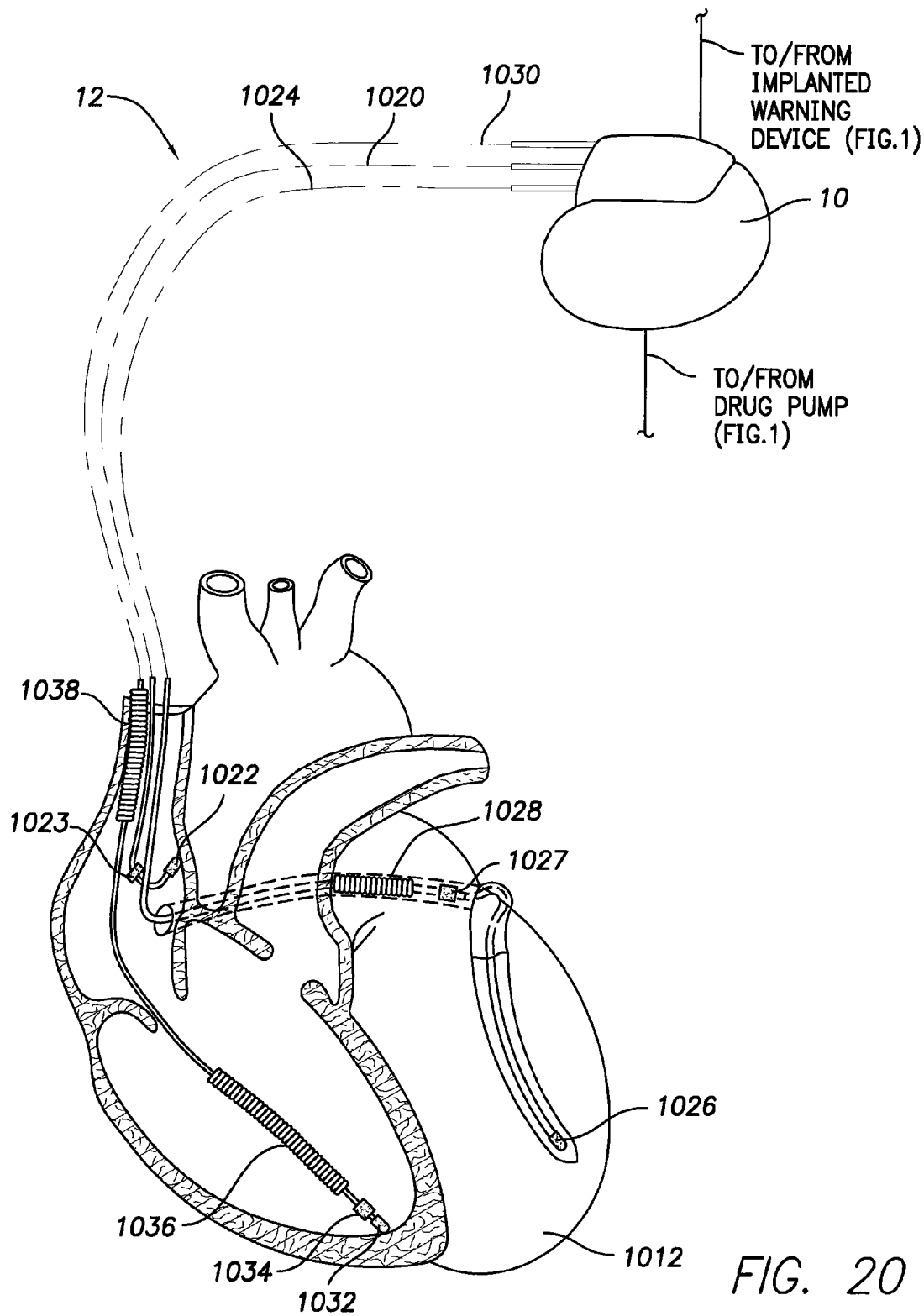
FIG. 20 is a simplified, partly cutaway view, illustrating the pacer/ICD of FIG. 1 along with a more complete set of leads implanted into the heart of the patient.

FIGS. 18 and 19 summarizes additional exemplary techniques, also performed in accordance the general method of FIG. 10, for distinguishing between ischemia and other conditions based on Tmax and Tend. Briefly, at step 800 of FIG. 18, the pacer/ICD or other device detects Tmax and Tend and, at step 802, determines the Tmax-Tend interval. If there is a substantial increase in the Tend–Tmax interval, then ischemia is suggested, at step 804. Otherwise, hypoglycemia, hyperglycemia, some other systemic condition, or normal conditions are suggested, at step 806. Turning now to FIG. 19, at step 900, the pacer/ICD or other device measures ST elevation and the Tend–Tmax interval and, at step 902, determines whether there has been a substantial change in ST elevation. If so, the device then further determines, at step 904, whether there has been a substantial increase in the Tend–Tmax interval. If so, then ischemia is suggested, at step 906. If not, then hypoglycemia or hyperglycemia is suggested, at step 908. If the no significant change in ST segment elevation was initially detected at step 902, then normal conditions are presumed, at step 904. Thus, with this technique, the pacer/ICD prioritizes the analysis. ST segment elevation is evaluated first and, if no significant change is observed, then the Tend–Tmax interval is not examined. Also, with this technique, the pacer/ICD does not seek to further distinguish between hyperglycemia and hypoglycemia as in FIG. 15.

What have been described are various techniques for detecting various abnormal physiological conditions within a patient. For the sake of completeness, a description of an exemplary pacer/ICD will now be provided. As many patients who suffer from cardiac ischemia and other abnormal physiological conditions are also candidates for pacer/ICDs, it is advantageous to configure a pacer/ICD to serve as the controller of the abnormal physiological detection system. The techniques of the invention, however, may be performed using any suitable implantable components.

Exemplary Pacer/ICD

FIG. 20 provides a simplified block diagram of the pacer/ICD of FIG. 1, which is a dual-chamber stimulation device capable of treating both fast and slow arrhythmias with stimulation therapy, including cardioversion, defibrillation, and pacing stimulation, as well as capable of detecting cardiac ischemia and/or other abnormal physiological conditions and for controlling the delivery of therapy and warnings in response thereto. To provide atrial chamber pacing stimulation and sensing, pacer/ICD 10 is shown in electrical communication with a heart 1012 by way of a right atrial lead 1020 having an atrial tip electrode 1022 and an atrial ring electrode 1023 implanted in the atrial appendage. Pacer/ICD 10 is also in electrical communication with the heart by way of a right ventricular lead 1030 having, in this embodiment, a ventricular tip electrode 1032, a right ventricular ring electrode 1034, a right ventricular (RV) coil electrode 1036, and a SVC coil electrode 1038. Typically, the right ventricular lead 1030 is transvenously inserted into the heart so as to place the RV coil electrode 1036 in the right ventricular apex, and the SVC coil electrode 1038 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a "coronary sinus" lead 1024 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 1024 is designed to receive atrial and ventricular cardiac signals and to deliver left ventricular pacing therapy using at least a left ventricular tip electrode 1026, left atrial pacing therapy using at least a left atrial ring electrode 1027, and shocking therapy using at least a left atrial coil electrode 1028. With this configuration, biventricular pacing can be performed. Although only three leads are shown in FIG. 20, it should also be understood that additional stimulation leads (with one or more pacing, sensing and/or shocking electrodes) may be used in order to efficiently and effectively provide pacing stimulation to the left side of the heart or atrial cardioversion and/or defibrillation.

Figure 21:
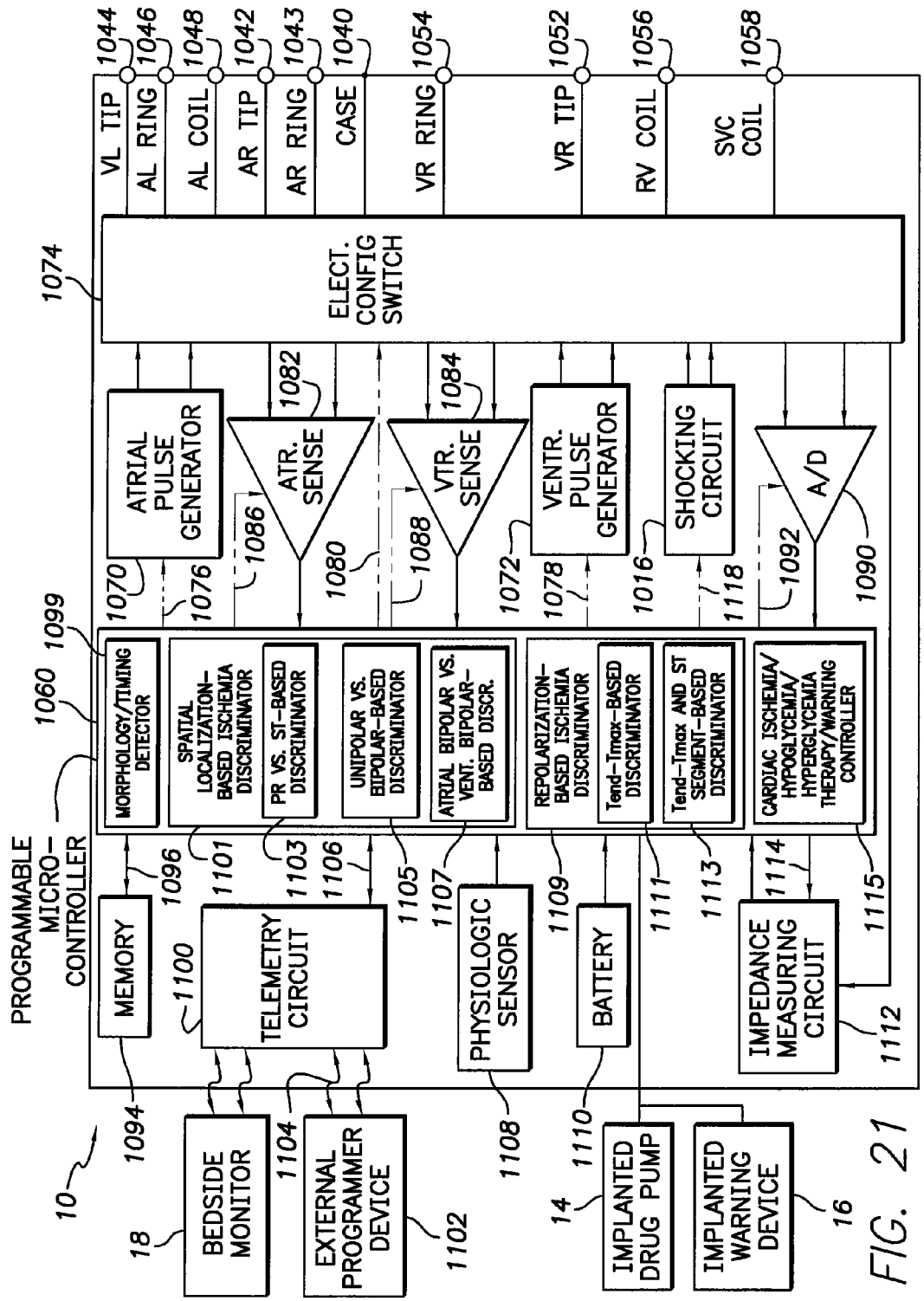
FIG. 21 is a functional block diagram of the pacer/ICD of FIG. 20, illustrating basic circuit elements that provide cardioversion, defibrillation and/or pacing stimulation in the heart and particularly illustrating components for performing the techniques of FIGS. 2-19.

A simplified block diagram of internal components of pacer/ICD 10 is shown in FIG. 21. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned apnea detection and therapy. The housing 1040 for pacer/ICD 10, shown schematically in FIG. 21, is often referred to as the "can", "case" or "case electrode" and may be programmably selected to act as the return electrode for all "unipolar" modes. The housing 1040 may further be used as a return electrode alone or in combination with one or more of the coil electrodes, 1028, 1036 and 1038, for shocking purposes. The housing 1040 further includes a connector (not shown) having a plurality of terminals, 1042, 1043, 1044, 1046, 1048, 1052, 1054, 1056 and 1058 (shown schematically and, for convenience, the names of the electrodes to which they are connected are shown next to the terminals). As such, to achieve right atrial sensing and pacing, the connector includes at least a right atrial tip terminal ($A_R$ TIP) 1042 adapted for connection to the atrial tip electrode 1022 and a right atrial ring ($A_R$ RING) electrode 1043 adapted for connection to right atrial ring electrode 1023. To achieve left chamber sensing, pacing and shocking, the connector includes at least a left ventricular tip terminal ($V_L$ TIP) 1044, a left atrial ring terminal ($A_L$ RING) 1046, and a left atrial shocking terminal ($A_L$ COIL) 1048, which are adapted for connection to the left ventricular ring electrode 1026, the left atrial tip electrode 1027, and the left atrial coil electrode 1028, respectively. To support right chamber sensing, pacing and shocking, the connector further includes a right ventricular tip terminal ($V_R$ TIP) 1052, a right ventricular ring terminal ($V_R$ RING) 1054, a right ventricular shocking terminal ($R_V$ COIL) 1056, and an SVC shocking terminal (SVC COIL) 1058, which are adapted for connection to the right ventricular tip electrode 1032, right ventricular ring electrode 1034, the RV coil electrode 1036, and the SVC coil electrode 1038, respectively.

At the core of pacer/ICD 10 is a programmable microcontroller 1060, which controls the various modes of stimulation therapy. As is well known in the art, the microcontroller 1060 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 1060 includes the ability to process or monitor input signals (data) as controlled by a program code stored in a designated block of memory. The details of the design and operation of the microcontroller 1060 itself are not critical to the invention. Rather, any suitable microcontroller 1060 may be used that carries out the functions described herein. The use of microprocessor-based control circuits for performing timing and data analysis functions are well known in the art.

As shown in FIG. 21, an atrial pulse generator 1070 and a ventricular/impedance pulse generator 1072 generate pacing stimulation pulses for delivery by the right atrial lead 1020, the right ventricular lead 1030, and/or the coronary sinus lead 1024 via an electrode configuration switch 1074. It is understood that in order to provide stimulation therapy in each of the four chambers of the heart, the atrial and ventricular pulse generators, 1070 and 1072, may include dedicated, independent pulse generators, multiplexed pulse generators or shared pulse generators. The pulse generators, 1070 and 1072, are controlled by the microcontroller 1060 via appropriate control signals, 1076 and 1078, respectively, to trigger or inhibit the stimulation pulses.

The microcontroller 1060 further includes timing control circuitry 1079 used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 1074 includes a plurality of switches for connecting the desired electrodes to the appropriate I/O circuits, thereby providing complete electrode programmability. Accordingly, the switch 1074, in response to a control signal 1080 from the microcontroller 1060, determines the polarity of the stimulation pulses (e.g., unipolar, bipolar, combipolar, etc.) by selectively closing the appropriate combination of switches (not shown) as is known in the art.

Atrial sensing circuits 1082 and ventricular sensing circuits 1084 may also be selectively coupled to the right atrial lead 1020, coronary sinus lead 1024, and the right ventricular lead 1030, through the switch 1074 for detecting the presence of cardiac activity in each of the four chambers of the heart. Accordingly, the atrial (ATR. SENSE) and ventricular (VTR. SENSE) sensing circuits, 1082 and 1084, may include dedicated sense amplifiers, multiplexed amplifiers or shared amplifiers. The switch 1074 determines the "sensing polarity" of the cardiac signal by selectively closing the appropriate switches, as is also known in the art. In this way, the clinician may program the sensing polarity independent of the stimulation polarity. Each sensing circuit, 1082 and 1084, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 1082 and 1084, are connected to the microcontroller 1060 which, in turn, are able to trigger or inhibit the atrial and ventricular pulse generators, 1070 and 1072, respectively, in a demand fashion in response to the absence or presence of cardiac activity in the appropriate chambers of the heart.

For arrhythmia detection, pacer/ICD 10 utilizes the atrial and ventricular sensing circuits, 1082 and 1084, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 1060 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 1090. The data acquisition system 1090 is configured to acquire intracardiac electrogram signals, convert the raw analog data into a digital signal, and store the digital signals for later processing and/or telemetric transmission to an external device 1102. The data acquisition system 1090 is coupled to the right atrial lead 1020, the coronary sinus lead 1024, and the right ventricular lead 1030 through the switch 1074 to sample cardiac signals across any pair of desired electrodes. The microcontroller 1060 is further coupled to a memory 1094 by a suitable data/address bus 1096, wherein the programmable operating parameters used by the microcontroller 1060 are stored and modified, as required, in order to customize the operation of pacer/ICD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 1094 through a telemetry circuit 1100 in telemetric communication with the external device 1102, such as a programmer, transtelephonic transceiver or a diagnostic system analyzer. The telemetry circuit 1100 is activated by the microcontroller by a control signal 1106. The telemetry circuit 1100 advantageously allows intracardiac electrograms and status information relating to the operation of pacer/ICD 10 (as contained in the microcontroller 1060 or memory 1094) to be sent to the external device 1102 through an established communication link 1104. Pacer/ICD 10 further includes an accelerometer or other physiologic sensor 1108, commonly referred to as a "rate-responsive" sensor because it is typically used to adjust pacing stimulation rate according to the exercise state of the patient. However, the physiological sensor 1108 may further be used to detect changes in cardiac output, changes in the physiological condition of the heart, or diurnal changes in activity (e.g., detecting sleep and wake states) and to detect arousal from sleep. Accordingly, the microcontroller 1060 responds by adjusting the various pacing parameters (such as rate, AV Delay, V-V Delay, etc.) at which the atrial and ventricular pulse generators, 1070 and 1072, generate stimulation pulses. While shown as being included within pacer/ICD 10, it is to be understood that the physiologic sensor 1108 may also be external to pacer/ICD 10, yet still be implanted within or carried by the patient. A common type of rate responsive sensor is an activity sensor incorporating an accelerometer or a piezoelectric crystal, which is mounted within the housing 1040 of pacer/ICD 10. Other types of physiologic sensors are also known, for example, sensors that sense the oxygen content of blood, respiration rate and/or minute ventilation, pH of blood, ventricular gradient, patient posture, LAP, arterial BP, stroke volume, cardiac output, etc.

The pacer/ICD additionally includes at least one battery 1110 of other power source, which provides operating power to all of the circuits shown in FIG. 21. The battery 1110 may vary depending on the capabilities of pacer/ICD 10. If the system only provides low voltage therapy, a lithium iodine or lithium copper fluoride cell may be utilized. For pacer/ICD 10, which employs shocking therapy, the battery 1110 must be capable of operating at low current drains for long periods, and then be capable of providing high-current pulses (for capacitor charging) when the patient requires a shock pulse. The battery 1110 must also have a predictable discharge characteristic so that elective replacement time can be detected. Accordingly, pacer/ICD 10 is preferably capable of high voltage therapy and appropriate batteries.

As further shown in FIG. 21, pacer/ICD 10 includes an impedance measuring circuit 1112 that is enabled by the microcontroller 1060 via a control signal 1114. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 1112 is advantageously coupled to the switch 74 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 1060 further controls a shocking circuit 1116 by way of a control signal 1118. The shocking circuit 1116 generates shocking pulses of low (up to 0.5 joules), moderate (0.5-10 joules) or high energy (11 to 40 joules), as controlled by the microcontroller 1060. Such shocking pulses are applied to the heart of the patient through at least two shocking electrodes, and as shown in this embodiment, selected from the left atrial coil electrode 1028, the RV coil electrode 1036, and/or the SVC coil electrode 1038. The housing 1040 may act as an active electrode in combination with the RV electrode 1036, or as part of a split electrical vector using the SVC coil electrode 1038 or the left atrial coil electrode 1028 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 10-40 joules), delivered asynchronously (since R-waves may be too disorganized), and pertaining exclusively to the treatment of fibrillation. Accordingly, the microcontroller 1060 is capable of controlling the synchronous or asynchronous delivery of the shocking pulses.

Microcontroller 1060 also includes various components directed to the detecting cardiac ischemia and discriminating ischemia from various systemic conditions or influences and for controlling delivery of therapy and warnings in response thereto. In particular, the microcontroller includes a morphology/timing detector 1099, which includes a morphological feature detection unit operative to detect morphological features of electrical cardiac signals indicative of possible cardiac ischemia within the patient and also a timing unit operative to track various timing intervals including repolarization-based intervals between the peaks of T-waves and the ends of T-waves within electrical cardiac signals. The microcontroller also includes a spatial localization-based ischemia discriminator 1101 operative to detect cardiac ischemia and distinguish ischemia from other conditions based, at least in part, on the spatial localization of changes in morphological features of cardiac signals using, e.g., the techniques of FIG. 2. In this example, discriminator 1101 includes a PR vs. ST segment-based ischemia discriminator 1103 operative to discriminate cardiac ischemia from other conditions based on changes PR and ST segments of cardiac signals using, e.g., the techniques of FIG. 3. Discriminator 1101 also includes a unipolar vs. bipolar-based ischemia discriminator 1105 operative to discriminate cardiac ischemia from other conditions based on differences between cardiac signals sensed based on various combinations of unipolar ("global") and bipolar ("local") electrode pairs using, e.g., the techniques of FIG. 8. Still further, discriminator 1101 also includes a atrial bipolar vs. unipolar bipolar-based ischemia discriminator 1107 operative to discriminate cardiac ischemia from other conditions based on differences between cardiac signals sensed based on various combinations of "local" bipolar signals sensed in different regions of the heart using, e.g., the techniques of FIG. 9.

Microcontroller 1060 additionally includes a repolarization-based ischemia discriminator 1109 operative to detect cardiac ischemia and distinguish ischemia from other conditions based, at least in part, on selected repolarization intervals using, e.g., the techniques of FIG. 10. In this example, discriminator 1109 includes a Tend–Tmax-based ischemia discriminator 1111 operative to discriminate cardiac ischemia from other conditions based on changes in the Tend–Tmax interval using, e.g., the techniques of FIG. 11 or FIG. 18. Discriminator 1109 also includes a Tend–Tmax and ST segment-based ischemia discriminator 1113 operative to discriminate cardiac ischemia from other conditions based on changes in the Tend–Tmax interval and the ST segment elevation using, e.g., the techniques of FIG. 1115 or FIG. 19. A cardiac ischemia/hypoglycemia/hyperglycemia therapy/warning controller 1115 controls delivery of therapy and/or warning signals in response to the detection of ischemia, hypoglycemia, and/or hyperglycemia or other abnormal medical conditions, again in accordance with techniques already described. Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, as hardware devices.

In general, a wide variety of techniques can be implemented consistent with the principles the invention and no attempt is made herein to describe all possible techniques. Although described primarily with reference to an example wherein the implanted device is a pacer/ICD, principles of the invention are applicable to other implantable medical devices as well. In addition, whereas many of the techniques described herein are performed by the implanted device, the techniques may alternatively be performed by an external device using IEGM signals or other signals transmitted from the implanted device. For example, a bedside monitor may be configured to receive IEGM signals from the implanted device via "long-range" telemetry then analyze the signals using the aforementioned techniques and issue any appropriate warnings. Alternatively, the bedside monitor may transmit the IEGM data to a central server or other central processing device, which analyzes data from multiple patients to detect ischemia or other conditions within any of those patients. In such an implementation, the central processing device then transmits appropriate warning signals to the bedside monitor of the patient for warning the patient and additionally transmits appropriate warning signals to the physician associated with the patient or a third party such as emergency medical service (EMS) personnel.

The various functional components of the exemplary systems described herein may be implemented using any appropriate technology including, for example, microprocessors running software programs or application specific integrated circuits (ASICs) executing hard-wired logic operations. The exemplary embodiments of the invention described herein are merely illustrative of the invention and should not be construed as limiting the scope of the invention. Note also that the term "including" as used herein is intended to be inclusive, i.e. "including but not limited to."

What is claimed is:

1. A method, for use with an implantable medical device, for distinguishing cardiac ischemia from other conditions affecting a morphology of electrical cardiac signals sensed within a patient in which the device is implanted, the method comprising:
   monitoring electrical cardiac signals from a plurality of spatially-distinct locations within a heart of the patient;
   detecting changes in morphological features of the electrical cardiac signals indicative of possible cardiac ischemia within the patient;
   determining whether the changes in the morphological features are the result of spatially localized changes within a portion of the heart by:
      determining that the changes in the detected morphological features are global if the changes are detected in signals detected at each of the plurality of spatially-distinct locations; and
      determining that the changes in the detected morphological features are local if the changes are detected in signals detected at one or more, but not all, of the plurality of spatially-distinct locations;
   determining that the changes in morphological features of the electrical cardiac signals indicate cardiac ischemia if the changes are determined to be local; and
   determining that the changes in morphological features of the electrical cardiac signals indicate systemic influences if the changes are determined to be global.

2. The method of claim 1 wherein determining whether the changes in the morphological features are the result of spatially localized changes within a portion of the heart further comprises:
   determining whether changes in the detected features indicative of cardiac ischemia are manifest both in features affected by atrial repolarization and in features affected by ventricular repolarization;
   determining that the changes in the detected features are global if changes are detected both in features affected by atrial repolarization and in features affected by ventricular repolarization; and
   determining that the changes in the detected features are local if the changes are manifest in either the features affected by atrial repolarization or in the features affected by ventricular repolarization, but not both.

3. The method of claim 2 wherein features affected by atrial repolarization include an amplitude of a PR segment of an intracardiac electrogram (IEGM) and wherein features affected by ventricular repolarization include an amplitude of an ST segment of the IEGM and parameters representative of T-wave morphology.

4. The method of claim 2 wherein features affected by ventricular repolarization include parameters representative of T-wave morphology.

5. The method of claim 2, wherein determining whether the changes in the morphological features are a result of spatially localized changes within a portion of the heart further comprises:
   determining whether changes in the detected features indicative of cardiac ischemia are manifest both in signals sensed locally at a first location in the heart using a first pair of bipolar electrodes and at a second, different location in the heart using a second pair of bipolar electrodes;
   determining that the changes in the detected features are global if significant changes are detected in the signals sensed locally at the first location and in the signals sensed at the second locations; and
   determining that the changes in the detected features are local if significant changes are detected either in the signals sensed locally at the first location, or in the signals sensed locally at the second location, but not both.

6. The method of claim 5 wherein the first location is in an atrium and the second location is in a ventricle.

7. The method of claim 5 wherein the features indicative of cardiac ischemia include an amplitude of an ST segment of an intracardiac electrogram (IEGM).

8. The method of claim 7
wherein the changes in the detected features are determined to be global if substantially equal changes occur in the amplitude of the ST segment as detected in the signals sensed at the first and second locations; and wherein the changes in the detected features are determined to be local if more significant changes occur in the amplitude of the ST segment as detected in signals sensed at one of the first and second locations as opposed to the other of the first and second locations.

9. The method of claim 7 wherein distinguishing cardiac ischemia from other conditions affecting the morphology of electrical cardiac signals further comprises:

generating a signal indicative of cardiac ischemia if the changes in the detected features are determined to be local; and generating a signal indicative of a systemic condition if the changes in the detected features are determined to be global.

10. The method of claim 1 further including controlling therapy in response to an episode of cardiac ischemia.

11. The method of claim 1 further comprising generating a warning signal in response to cardiac ischemia.

12. The method of claim 1, wherein determining that the changes in morphological features of the electrical cardiac signals indicate systemic influences further comprises:

detecting an episode of one or more of hypoglycemia, hyperglycemia, hypokalemia and hyperkalemia and controlling therapy in response to detecting one or more of hypoglycemia, hyperglycemia, hypokalemia and hyperkalemia.

13. The method of claim 12 further including generating a warning signal in response to detecting one or more of hypoglycemia, hyperglycemia, hypokalemia and hyperkalemia.

14. A system, for use with an implantable medical device, for distinguishing cardiac ischemia from other conditions affecting a morphology of electrical cardiac signals sensed within a patient in which the device is implanted, the system comprising:

a plurality of electrodes configured to monitor electrical cardiac signals from a plurality of spatially-distinct locations within a heart of the patient;

a morphological feature detecting unit operative to detect changes in morphological features of the electrical cardiac signals indicative of possible cardiac ischemia within the patient; and a cardiac ischemia discrimination unit configured to:
  determine that the changes in the detected morphological features are global if the changes are detected in signals detected at each of the plurality of spatially-distinct locations;
  determine that the changes in the detected morphological features are local if the changes are detected in signals detected at one or more, but not all, of the plurality of spatially-distinct locations;

wherein:
  when the changes in the detected morphological features are determined to be global, the cardiac ischemia discrimination unit is configured to determine that the changes in morphological features of the electrical cardiac signals indicate systemic influences; and
  when the changes in the detected morphological features are determined to be local, the cardiac ischemia discrimination unit is configured to determine that the changes in the morphological features of the electrical cardiac signals indicate cardiac ischemia.

15. A system, for use with an implantable medical device, for distinguishing cardiac ischemia from other conditions affecting a morphology of electrical cardiac signals sensed within a patient in which the device is implanted, the system comprising:

a plurality of electrodes configured to monitor electrical cardiac signals from a plurality of spatially-distinct locations within a heart of the patient;

a morphological feature detecting unit operative to detect changes in morphological features of the electrical cardiac signals indicative of possible cardiac ischemia within the patient;

a timing unit operative to track repolarization-based intervals of intervals between the peaks of T-waves and the ends of T-waves within the electrical cardiac signals; and a cardiac ischemia discrimination unit configured to:
  determine if the T-wave based intervals indicate a cardiac ischemia or systemic influences;
  determine that the changes in the detected morphological features are global if the changes are detected in signals detected at each of the plurality of spatially-distinct locations;
  determine that the changes in the detected morphological features are local if the changes are detected in signals detected at one or more, but not all, of the plurality of spatially-distinct locations;

wherein:
  when the changes in the detected morphological features are determined to be global and the T-wave based intervals indicate systemic influences, the cardiac ischemia discrimination unit is configured to determine that the changes in morphological features of the electrical cardiac signals indicate systemic influences; and
  when the changes in the detected morphological features are determined to be local and the T-wave based intervals indicate cardiac ischemia, the cardiac ischemia discrimination unit is configured to determine that the changes in the morphological features of the electrical cardiac signals indicate cardiac ischemia.

* * * * *